(12) United States Patent
Yates et al.

(10) Patent No.: US 9,161,803 B2
(45) Date of Patent: Oct. 20, 2015

(54) MOTOR DRIVEN ELECTROSURGICAL DEVICE WITH MECHANICAL AND ELECTRICAL FEEDBACK

(75) Inventors: David C. Yates, West Chester, OH (US); Aron O. Zingman, Cambridge, MA (US); Ashvani K. Madan, Mason, OH (US); Kevin L. Houser, Springboro, OH (US); Danius P. Silkaitis, Mason, OH (US); William D. Dannaher, Cincinnati, OH (US); Timothy G. Dietz, Terrace Park, OH (US); Richard W. Timm, Cincinnati, OH (US); Robert J. Laird, Morrow, OH (US); Gavin M. Monson, Oxford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 33 days.

(21) Appl. No.: 13/151,481

(22) Filed: Jun. 2, 2011

(65) Prior Publication Data

US 2012/0116379 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 18/14*     (2006.01)
*A61B 17/00*     (2006.01)
(Continued)

(52) U.S. Cl.
CPC ....... *A61B 18/1442* (2013.01); *A61B 17/00234* (2013.01); *A61B 17/320068* (2013.01);
(Continued)

(58) Field of Classification Search
USPC ..................................... 606/50–52
See application file for complete search history.

(56) References Cited

U.S. PATENT DOCUMENTS

| 1,754,806 A | 4/1930 | Stevenson |
| 3,297,192 A | 1/1967 | Swett |

(Continued)

FOREIGN PATENT DOCUMENTS

| DE | 102008051866 | 10/2010 |
| DE | 102009013034 | 10/2010 |

(Continued)

OTHER PUBLICATIONS

U.S. Appl. No. 12/576,776, Oct. 9, 2009, Boudreaux et al.
(Continued)

*Primary Examiner* — Jaymi Della

(57) ABSTRACT

An electrosurgical device comprises an end effector, a cutting member, and en electromechanical driver. The end effector comprises a pair of jaws that clamp tissue. The jaws include electrodes that deliver RF energy to clamped tissue. The cutting member cuts tissue clamped between the jaws. The electromechanical driver drives the cutting member. A control module commands the electromechanical driver, and regulates the delivery of RF energy to the electrodes, based on a combination of user input and feedback signals from the electrodes and from the electromechanical driver. The device may provide tactile feedback to the user through the user input feature, based on a load encountered by the cutting member. The device may alert the user when the exterior of end effector makes incidental contact with tissue, to avoid inadvertently burning the tissue. The device may include a removable battery pack to power the electromechanical driver and the electrodes.

1 Claim, 15 Drawing Sheets

(51) Int. Cl.
  *A61B 17/32* (2006.01)
  *A61B 18/00* (2006.01)
  *A61B 18/04* (2006.01)
  *H02J 7/00* (2006.01)
  *H01M 2/26* (2006.01)
  *H01M 2/10* (2006.01)
  *A61B 18/12* (2006.01)
  *A61B 19/00* (2006.01)
  *A61B 17/064* (2006.01)
  *A61B 17/285* (2006.01)
  *A61B 17/29* (2006.01)

(52) U.S. Cl.
  CPC ........ *A61B17/320092* (2013.01); *A61B 18/00* (2013.01); *A61B 18/04* (2013.01); *A61B 18/12* (2013.01); *A61B 18/14* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 19/38* (2013.01); *A61B 19/56* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | | |
|---|---|---|---|
| 3,419,198 A | | 12/1968 | Pettersen |
| 3,619,671 A | | 11/1971 | Shoh |
| 4,034,762 A | * | 7/1977 | Cosens et al. ............ 606/40 |
| 4,057,220 A | | 11/1977 | Kudlacek |
| 4,535,773 A | * | 8/1985 | Yoon ..................... 606/185 |
| 4,641,076 A | | 2/1987 | Linden et al. |
| 4,662,068 A | | 5/1987 | Polonsky |
| 4,666,037 A | | 5/1987 | Weissman |
| 4,717,018 A | | 1/1988 | Sacherer et al. |
| 4,717,050 A | | 1/1988 | Wright |
| 4,721,097 A | | 1/1988 | D'Amelio |
| 4,768,969 A | | 9/1988 | Bauer et al. |
| 4,800,878 A | | 1/1989 | Cartmell |
| 4,844,259 A | | 7/1989 | Glowczewskie, Jr. |
| 4,878,493 A | | 11/1989 | Pasternak et al. |
| 5,071,417 A | | 12/1991 | Sinofsky |
| 5,107,155 A | | 4/1992 | Yamaguchi |
| 5,144,771 A | | 9/1992 | Miwa |
| 5,169,733 A | | 12/1992 | Savovic et al. |
| 5,176,677 A | | 1/1993 | Wuchinich |
| 5,246,109 A | | 9/1993 | Markle et al. |
| 5,273,177 A | | 12/1993 | Campbell |
| 5,277,694 A | | 1/1994 | Leysieffer et al. |
| 5,308,358 A | | 5/1994 | Bond et al. |
| 5,322,055 A | | 6/1994 | Davison |
| 5,339,799 A | | 8/1994 | Kami et al. |
| 5,358,508 A | | 10/1994 | Cobb et al. |
| 5,361,902 A | | 11/1994 | Abidin et al. |
| 5,429,229 A | | 7/1995 | Chester et al. |
| 5,449,370 A | | 9/1995 | Vaitekumas |
| 5,454,378 A | | 10/1995 | Palmer et al. |
| 5,501,607 A | | 3/1996 | Yoshioka et al. |
| 5,507,297 A | | 4/1996 | Slater et al. |
| 5,561,881 A | | 10/1996 | Klinger et al. |
| 5,578,052 A | | 11/1996 | Koros et al. |
| 5,580,258 A | | 12/1996 | Wakata |
| 5,582,617 A | | 12/1996 | Klieman et al. |
| 5,590,778 A | | 1/1997 | Dutchik |
| 5,592,065 A | | 1/1997 | Oglesbee et al. |
| 5,597,531 A | | 1/1997 | Liberti et al. |
| 5,599,350 A | * | 2/1997 | Schulze et al. ............ 606/51 |
| 5,630,420 A | | 5/1997 | Vaitekunas |
| 5,630,456 A | | 5/1997 | Hugo et al. |
| 5,690,222 A | | 11/1997 | Peters |
| 5,741,305 A | | 4/1998 | Vincent et al. |
| 5,776,155 A | | 7/1998 | Beaupre et al. |
| 5,800,336 A | | 9/1998 | Ball et al. |
| 5,817,128 A | | 10/1998 | Storz |
| 5,868,244 A | | 2/1999 | Ivanov et al. |
| 5,873,873 A | | 2/1999 | Smith et al. |
| 5,882,310 A | | 3/1999 | Marian, Jr. |
| 5,935,144 A | | 8/1999 | Estabrook |
| 5,938,633 A | | 8/1999 | Beaupre |
| 5,944,737 A | | 8/1999 | Tsonton et al. |
| 5,951,575 A | | 9/1999 | Bolduc et al. |
| 5,957,961 A | * | 9/1999 | Maguire et al. ............ 607/99 |
| 5,980,510 A | | 11/1999 | Tsonton et al. |
| 5,997,531 A | | 12/1999 | Loeb et al. |
| 6,018,227 A | | 1/2000 | Kumar et al. |
| 6,051,010 A | | 4/2000 | DiMatteo et al. |
| 6,056,735 A | | 5/2000 | Okada et al. |
| 6,063,098 A | | 5/2000 | Houser et al. |
| 6,066,151 A | | 5/2000 | Miyawaki et al. |
| 6,083,191 A | | 7/2000 | Rose |
| 6,099,537 A | | 8/2000 | Sugai et al. |
| 6,165,191 A | | 12/2000 | Shibata et al. |
| 6,204,592 B1 | | 3/2001 | Hur |
| 6,214,023 B1 | | 4/2001 | Whipple et al. |
| 6,246,896 B1 | | 6/2001 | Dumoulin et al. |
| 6,248,238 B1 | | 6/2001 | Burtin et al. |
| 6,325,811 B1 | | 12/2001 | Messerly |
| 6,339,368 B1 | | 1/2002 | Leith |
| 6,398,755 B1 | | 6/2002 | Belef et al. |
| 6,409,742 B1 | | 6/2002 | Fulton, III et al. |
| 6,500,176 B1 | | 12/2002 | Truckai et al. |
| 6,500,188 B2 | | 12/2002 | Harper et al. |
| 6,514,267 B2 | | 2/2003 | Jewett |
| 6,520,185 B1 | | 2/2003 | Bommannan et al. |
| 6,561,983 B2 | | 5/2003 | Cronin et al. |
| 6,609,414 B2 | | 8/2003 | Mayer et al. |
| 6,623,500 B1 | | 9/2003 | Cook et al. |
| 6,626,901 B1 | | 9/2003 | Treat et al. |
| 6,647,281 B2 | | 11/2003 | Morency |
| 6,650,975 B2 | | 11/2003 | Ruffner |
| 6,658,301 B2 | | 12/2003 | Loeb et al. |
| 6,666,875 B1 | | 12/2003 | Sakurai et al. |
| 6,717,193 B2 | | 4/2004 | Olewine et al. |
| 6,730,042 B2 | | 5/2004 | Fulton et al. |
| 6,758,855 B2 | | 7/2004 | Fulton, III et al. |
| 6,761,698 B2 | | 7/2004 | Shibata et al. |
| 6,783,524 B2 | | 8/2004 | Anderson et al. |
| 6,815,206 B2 | | 11/2004 | Lin et al. |
| 6,821,671 B2 | | 11/2004 | Hinton et al. |
| 6,838,862 B2 | | 1/2005 | Luu |
| 6,860,880 B2 | | 3/2005 | Treat et al. |
| 6,869,435 B2 | | 3/2005 | Blake |
| 6,923,807 B2 | | 8/2005 | Ryan et al. |
| 6,982,696 B1 | | 1/2006 | Shahoian |
| 7,031,155 B2 | | 4/2006 | Sauciuc et al. |
| 7,077,853 B2 | | 7/2006 | Kramer et al. |
| 7,083,589 B2 | | 8/2006 | Banko et al. |
| 7,112,201 B2 | | 9/2006 | Truckai et al. |
| 7,125,409 B2 | | 10/2006 | Truckai et al. |
| 7,150,712 B2 | | 12/2006 | Buehlmann et al. |
| 7,169,146 B2 | | 1/2007 | Truckai et al. |
| 7,186,253 B2 | | 3/2007 | Truckai et al. |
| 7,189,233 B2 | | 3/2007 | Truckai et al. |

(56) References Cited

U.S. PATENT DOCUMENTS

| | | | |
|---|---|---|---|
| 7,220,951 B2 | 5/2007 | Truckai et al. |
| 7,221,216 B2 | 5/2007 | Nguyen |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Kitahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0115997 A1* | 8/2002 | Truckai et al. ............ 606/51 |
| 2002/0165577 A1 | 11/2002 | Witt et al. |
| 2003/0018331 A1* | 1/2003 | Dycus et al. ............ 606/48 |
| 2003/0093103 A1 | 5/2003 | Malackowski et al. |
| 2003/0109802 A1 | 6/2003 | Laeseke et al. |
| 2003/0114851 A1* | 6/2003 | Truckai et al. ............ 606/51 |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0113827 A1* | 5/2005 | Dumbauld et al. ............ 606/45 |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2006/0293654 A1* | 12/2006 | Morrison et al. ............ 606/41 |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0175962 A1* | 8/2007 | Shelton et al. ............ 227/178.1 |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1* | 11/2007 | Edelstein et al. ............ 606/37 |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1* | 3/2009 | Baker ............ 606/51 |
| 2009/0105750 A1 | 4/2009 | Price et al. |
| 2009/0125026 A1* | 5/2009 | Rioux et al. ............ 606/45 |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0171354 A1* | 7/2009 | Deville et al. ............ 606/51 |
| 2009/0209979 A1 | 8/2009 | Yates et al. |
| 2009/0209990 A1* | 8/2009 | Yates et al. ............ 606/169 |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0274244 A1* | 10/2010 | Heard ............ 606/45 |
| 2010/0301095 A1 | 12/2010 | Shelton, IV et al. |

(56) References Cited

U.S. PATENT DOCUMENTS

| | | | |
|---|---|---|---|
| 2011/0009694 A1 | 1/2011 | Schultz et al. | |
| 2011/0015660 A1 | 1/2011 | Wiener et al. | |
| 2011/0058982 A1 | 3/2011 | Kaneko et al. | |
| 2011/0077514 A1 | 3/2011 | Ulric et al. | |
| 2011/0087212 A1 | 4/2011 | Aldridge et al. | |
| 2011/0152901 A1 | 6/2011 | Woodruff et al. | |
| 2011/0224668 A1* | 9/2011 | Johnson et al. | 606/42 |
| 2011/0247952 A1 | 10/2011 | Hebach et al. | |
| 2012/0179036 A1 | 7/2012 | Patrick et al. | |
| 2012/0265230 A1 | 10/2012 | Yates et al. | |
| 2012/0283732 A1 | 11/2012 | Lam | |
| 2012/0292367 A1 | 11/2012 | Morgan et al. | |
| 2013/0085330 A1 | 4/2013 | Ramamurthy et al. | |
| 2013/0085332 A1 | 4/2013 | Ramamurthy et al. | |
| 2013/0085397 A1 | 4/2013 | Ramamurthy et al. | |
| 2013/0090528 A1 | 4/2013 | Ramamurthy et al. | |
| 2013/0090530 A1 | 4/2013 | Ramamurthy et al. | |
| 2013/0090552 A1 | 4/2013 | Ramamurthy et al. | |
| 2013/0116690 A1 | 5/2013 | Unger et al. | |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 181021 A1 | 8/2007 |
| EP | 1839599 | 10/2007 |
| EP | 186275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,471, Jun. 2, 2011, Stulen et al.
U.S. Appl. No. 13/151,488, Jun. 2, 2011, Shelton IV et al.
U.S. Appl. No. 13/151,498, Jun. 2, 2011, Felder et al.
U.S. Appl. No. 13/151,503, Jun. 2, 2011, Madan et al.
U.S. Appl. No. 13/151,509, Jun. 2, 2011, Smith et al.
U.S. Appl. No. 13/151,512, Jun. 2, 2011, Houser et al.
U.S. Appl. No. 13/151,515, Jun. 2, 2011, Felder et al.
U.S. Appl. No. 13/176,875, Jul. 6, 2011, Smith et al.
U.S. Appl. No. 13/269,870, Oct. 10, 2011, Houser et al.
U.S. Appl. No. 13/269,883, Oct. 10, 2011, Mumaw et al.
U.S. Appl. No. 13/269,899, Oct. 10, 2011, Boudreaux et al.
U.S. Appl. No. 13/270,667, Oct. 11, 2011, Timm et al.
U.S. Appl. No. 13/270,684, Oct. 11, 2011, Madan et al.
U.S. Appl. No. 13/270,701, Oct. 11, 2011, Johnson et al.
U.S. Appl. No. 13/271,352, Oct. 12, 2011, Houser et al.
U.S. Appl. No. 13/271,364, Oct. 12, 2011, Houser et al.
U.S. Appl. No. 13/274,480, Oct. 17, 2011, Mumaw et al.
U.S. Appl. No. 13/274,496, Oct. 17, 2011, Houser et al.
U.S. Appl. No. 13/274,507, Oct. 17, 2011, Houser et al.
U.S. Appl. No. 13/274,516, Oct. 17, 2011, Haberstich et al.
U.S. Appl. No. 13/274,540, Oct. 17, 2011, Madan.
U.S. Appl. No. 13/274,805, Oct. 17, 2011, Price et al.
U.S. Appl. No. 13/274,830, Oct. 17, 2011, Houser et al.
U.S. Appl. No. 13/275,495, Oct. 18, 2011, Houser et al.
U.S. Appl. No. 13/275,514, Oct. 18, 2011, Houser et al.
U.S. Appl. No. 13/275,547, Oct. 18, 2011, Houser et al.
U.S. Appl. No. 13/275,563, Oct. 18, 2011, Houser et al.
U.S. Appl. No. 13/276,660, Oct. 19, 2011, Houser et al.
U.S. Appl. No. 13/276,673, Oct. 19, 2011, Kimball et al.
U.S. Appl. No. 13/276,687, Oct. 19, 2011, Price et al.
U.S. Appl. No. 13/276,707, Oct. 19, 2011, Houser et al.
U.S. Appl. No. 13/276,725, Oct. 19, 2011, Houser et al.
U.S. Appl. No. 13/276,745, Oct. 19, 2011, Stulen et al.
U.S. Appl. No. 13/277,328, Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997).pp. 433-436 (Abstract).
"System 6 Aseptic Battery System," Stryker (2006) pp. 1-2.
International Search Report and Written Opinion dated Jan. 26, 2012for Application No. PCT/US2011/059212.
International Search Report and Written Opinion dated Feb. 2, 2012for Application No.PCT/US2011/059378.
International Search Report dated Feb. 2, 2012for Application No. PCT/US2011/059354.
International Search Report dated Feb. 7, 2012 for Application No. PCT/US2011/059351.
International Search Report dated Feb. 13, 2012for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012for Application No. PCT/US2011/059362.
Communication from International Searching Authority dated Feb. 2, 2012for Application No. PCT/US2011/059222.
Communication from International Searching Authority dated Jan. 24, 2012 for Application No. PCT/US2011/059215.
Communication from International Searching Authority dated Feb. 2, 2012for Application No. PCT/US2011/059378.

(56) References Cited

OTHER PUBLICATIONS

Machine Translation of the Abstract of German Application No. DE 102009013034.
Machine Translation of German Application No. DE 102008051866.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
International Search Report dated Jan. 12, 2012 for Application No. PCT/US2011/059226.
International Search Report dated Jan. 26, 2012 for Application No. PCT/US2011/059220.
International Search Report dated Feb. 1, 2012 for Application No. PCT/US2011/059223.
International Search Report dated May 29, 2012 for Application No. PCT/US2011/059358.
International Search Report and Written Opinion dated Jul. 6, 2012 for Application No. PCT/US2011/059381.
Office Action Non-Final dated Aug. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Mar. 13, 2013 for U.S. Appl. No. 13/151,509.
Restriction Requirement dated Jun. 24, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Restriction Requirement dated Dec. 21, 2012 for U.S. Appl. No. 13/274,516.
Office Action Final dated Aug. 16, 2013 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non Final dated Feb. 14, 2014 for U.S. Appl. No. 13/274,480.
Restriction Requirement dated Dec. 9, 2013 for U.S. Appl. No. 13/274,496.
Office Action Final dated May 15, 2014 for U.S. Appl. No. 13/274,496.
Office Action Non-Final dated Feb. 6, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.

(56) References Cited

OTHER PUBLICATIONS

International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for Application No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.

* cited by examiner

MOTOR DRIVEN ELECTROSURGICAL DEVICE WITH MECHANICAL AND ELECTRICAL FEEDBACK

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

A variety of medical instruments have both moving components and electrical components. In some instances, the moving components are moved manually, such that electrical power that is provided to electrical components of the instrument is not also used to drive such manually moved components. Examples of such devices are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; and U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein. As described in greater detail below, any such devices may be modified to include a motor or other electrically powered device to drive an otherwise manually moved component.

In addition, many medical devices that rely on some form of electric power may be adapted to contain most, if not all, of the required components within the medical device. More specifically, some medical devices may be adapted to use an internal or attachable power source instead of requiring the device to be plugged into an external power source by a cable. Merely exemplary devices that may be adapted to include a portable power source include any of the devices described in the references cited above, among others. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
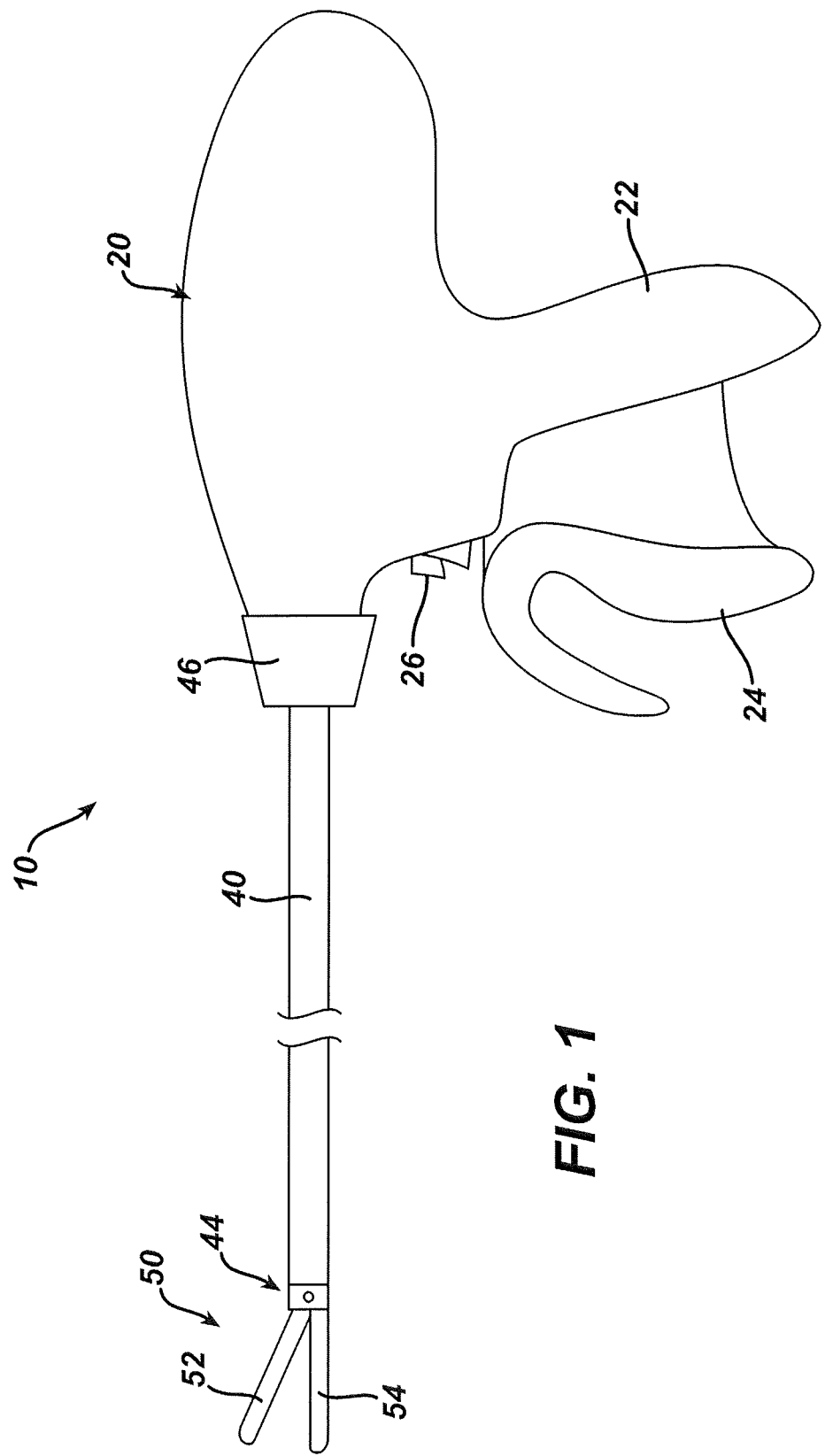
FIG. 1 depicts a side elevational view of an exemplary electrosurgical medical device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. Pat. No. 9,000,720, entitled "Medical Device Packaging with Charging Interface" issued Apr. 7, 2015; U.S. Pat. Pub. No. 2012/0111591, entitled "Packaging for Reclaimable Component of a Medical Device" published May 10, 2012; U.S. Pat. No. 9,017,851, entitled "Sterile Housing for Non-Sterile Medical Device Component" issued Apr. 28, 2015; U.S. Pat. Pub. No. 2012/0116380, entitled "Sterile Medical Instrument Charging Device" published May 10, 2012; U.S. Pat. No. 9,089,338, entitled "Medical Device Packaging with Window for Insertion of Reusable Component" issued Jul. 28, 2015; U.S. Pat. No. 9,072,523, entitled "Medical Device with Feature for Sterile Acceptance of Non-Sterile Reusable Component" issued Jul. 7, 2015; and U.S. Pat. Pub. No. 2012/0305427, entitled "Sterile Package System for Medical Device" published Dec. 6, 2012. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

I. EXEMPLARY ELECTROSURGICAL DEVICE WITH MOVABLE COMPONENT

FIGS. 1-6 show an exemplary electrosurgical device (10) that is constructed and operable in accordance with at least some of the teachings of U.S. Pat. No. 6,500,176 entitled "Electrosurgical Systems and Techniques for Sealing Tissue," issued Dec. 31, 2002, the disclosure of which is incorporated by reference herein. As described therein and as will be described in greater detail below, electrosurgical device (10) is operable to cut tissue and seal or weld tissue (e.g., a blood vessel, etc.) substantially simultaneously. In other words, electrosurgical device operates similar to an endocutter type of stapler, except that electrosurgical device provides tissue welding through application of bipolar RF energy instead of providing lines of staples to join tissue. It should also be understood that electrosurgical device (10) may have various structural and functional similarities with the ENSEAL® Tissue Sealing Device by Ethicon Endo-Surgery, Inc., of Cincinnati, Ohio. Furthermore, electrosurgical device (10) may have various structural and functional similarities with the devices taught in U.S. patent application Ser. No. 12/576,776, entitled "Surgical Instrument Comprising First and Second Drive Systems Actuatable by a Common Trigger Mechanism," filed Oct. 9, 2009, issued as U.S. Pat. No. 8,939, 974 on Jan. 27, 2015, the disclosure of which is incorporated by reference herein. To the extent that there is some degree of overlap between the teachings of U.S. Pat. No. 6,500,176, the ENSEAL® Tissue Sealing Device by Ethicon Endo-Surgery, Inc., of Cincinnati, Ohio, and/or U.S. patent application Ser. No. 12/576,776, issued as U.S. Pat. No. 8,939,974 on Jan. 27, 2015 and the following teachings relating to electrosurgical device (10), there is no intent for any of the following description to be presumed as admitted prior art. Several teachings below will in fact go beyond the scope of the teachings of U.S. Pat. No. 6,500,176, the ENSEAL® Tissue Sealing Device by Ethicon Endo-Surgery, Inc., of Cincinnati, Ohio, and U.S. patent application Ser. No. 12/576,776, issued as U.S. Pat. No. 8,939,974 on Jan. 27, 2015.

Figure 2:
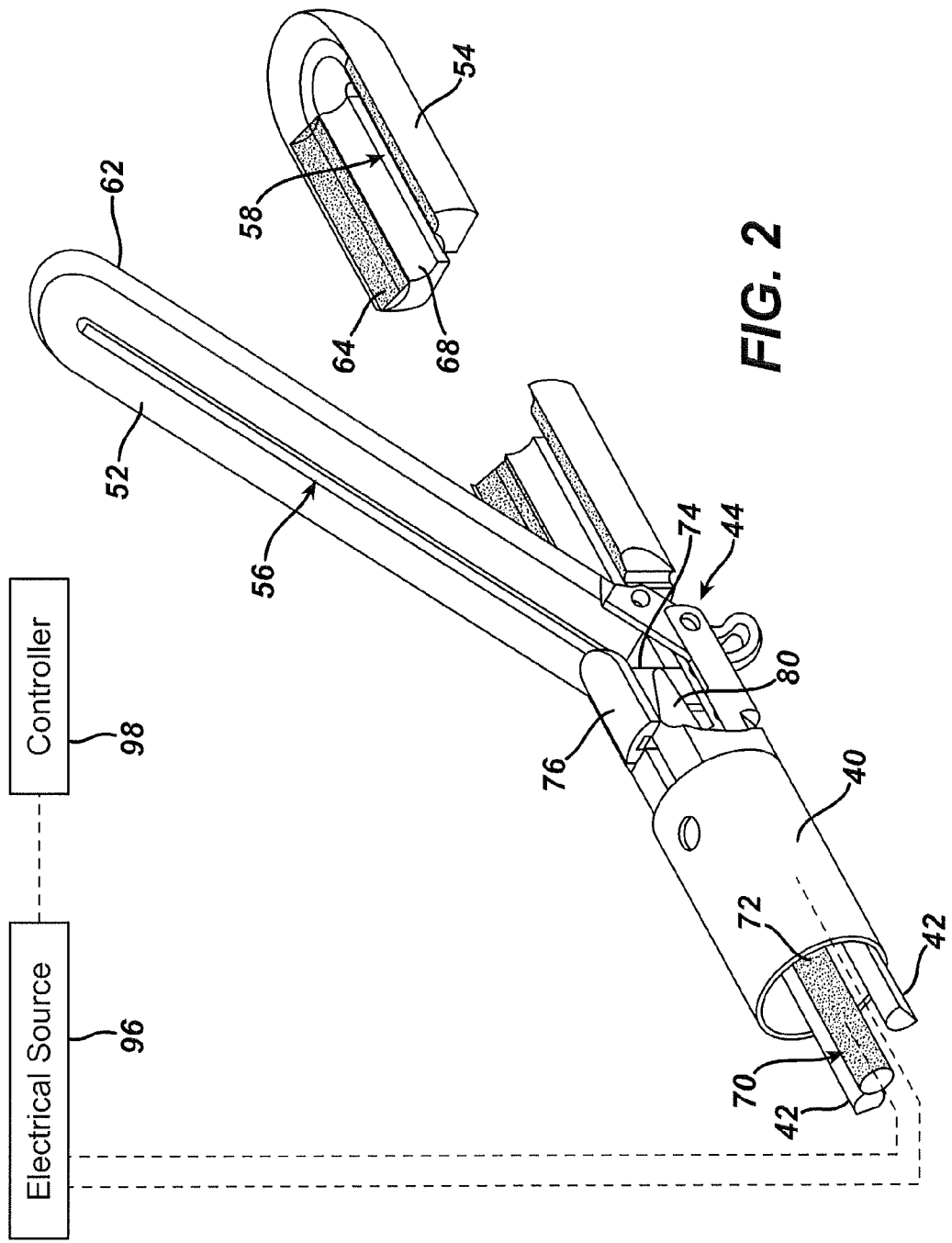
FIG. 2 depicts a perspective view of the end effector of the device of FIG. 1, in an open configuration.

Electrosurgical device (10) of the present example includes a handpiece (20), a shaft (40) extending distally from handpiece (20), and an end effector (50) disposed at a distal end of shaft (40). In some versions, shaft (40) is rotatable relative to handpiece (20) via a knob (46). In addition or in the alternative, shaft (40) may include an articulating section in some versions. End effector (50) comprises a first jaw (52) and a second jaw (54). In the present example, second jaw (54) is substantially fixed relative to shaft (40); while first jaw (52) pivots relative to shaft (40), toward and away from second jaw (52). In particular, as shown in FIG. 2, a pair of actuator rods (42) extend through shaft (40) and are joined with first jaw (52) at pivotal coupling (44), such that longitudinal movement of actuator rods (42) through shaft (40) provides pivoting of first jaw (52) relative to shaft (40) and relative to second jaw (54). Of course, jaws (52, 54) may instead have any other suitable kind of movement and may be actuated in any other suitable fashion. By way of example only, and as will be described in greater detail below, jaws (52, 54) may be actuated and thus closed by longitudinal translation of an elongate member (70), such that actuator rods (42) may simply be eliminated in some versions.

As best seen in FIGS. 2-5, first jaw (52) defines a longitudinally extending elongate slot (56); while second jaw (54) also defines a longitudinally extending elongate slot (58). In addition, the underside of first jaw (52) presents a first electrode surface (62); while the top side of second jaw (54) presents a second electrode surface (64). A partially cylindraceous recess (66) provides a transition from first electrode surface (62) to elongate slot (58) of first jaw (52). Similarly, a partially cylindraceous recess (68) provides a transition from second electrode surface (64) to elongate slot (58) of second jaw (54). As with other components and features referred to herein, cylindraceous recesses (66, 68) are merely optional. Electrode surfaces (64) are in communication with an electrical source (96) via one or more conductors (not shown) that extend along the length of shaft (40). Electrical source (96)

may be external to electrosurgical device (10) or may be integral with electrosurgical device (10) (e.g., in handpiece (20), etc.) as will be described in greater detail below.

With jaws (52, 54) in a closed position, shaft (40) and end effector (50) are sized and configured to fit through trocars having various inner diameters, such that electrosurgical device (10) is usable in minimally invasive surgery, though of course electrosurgical device (10) could also be used in open procedures if desired. By way of example only, with jaws (52, 54) in a closed position, shaft (40) and end effector (50) may present an outer diameter of approximately 5 mm. Alternatively, shaft (40) and end effector (50) may present any other suitable outer diameter.

Figure 3:
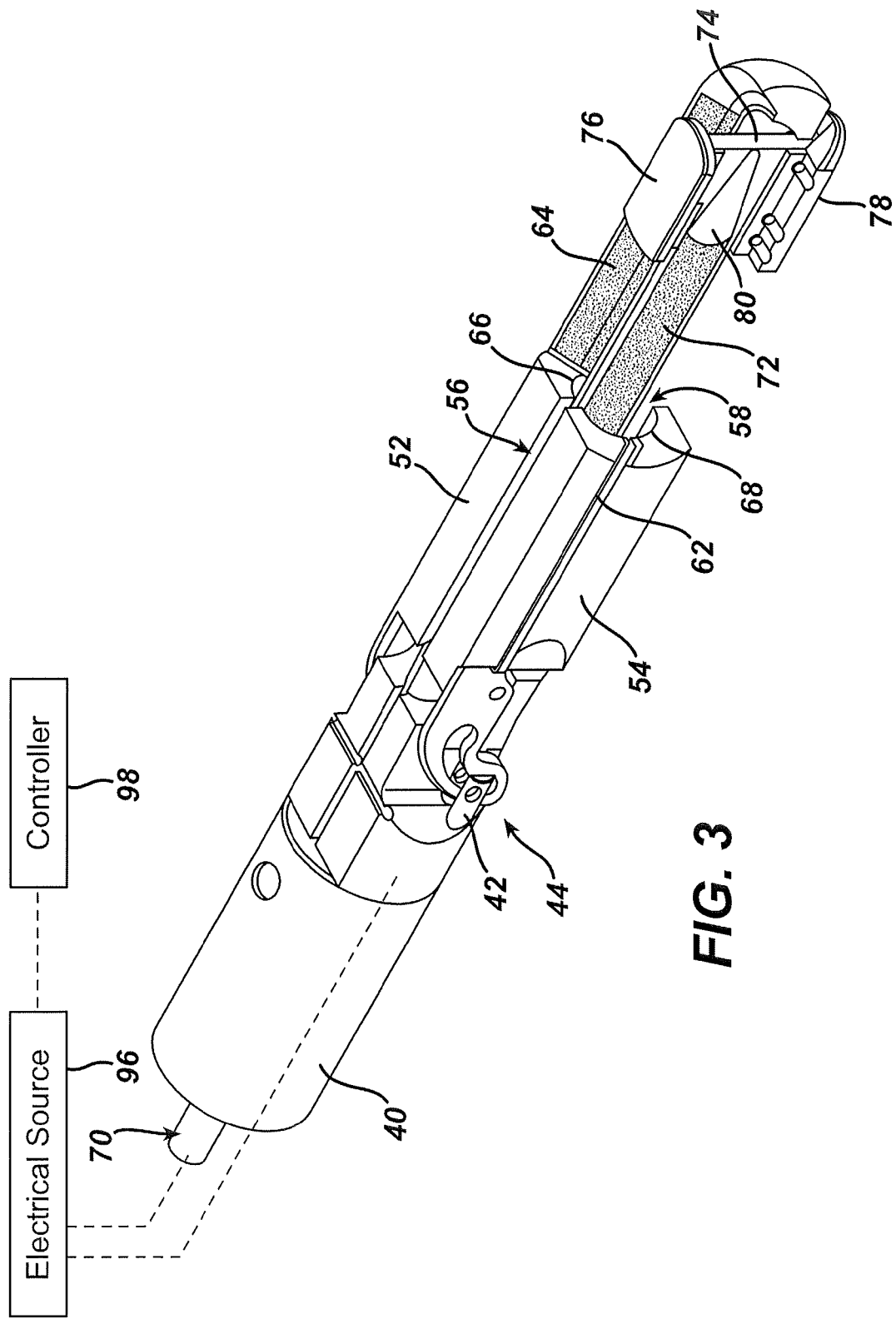
FIG. 3 depicts a perspective view of the end effector of FIG. 2, in a closed configuration.
Figure 4:
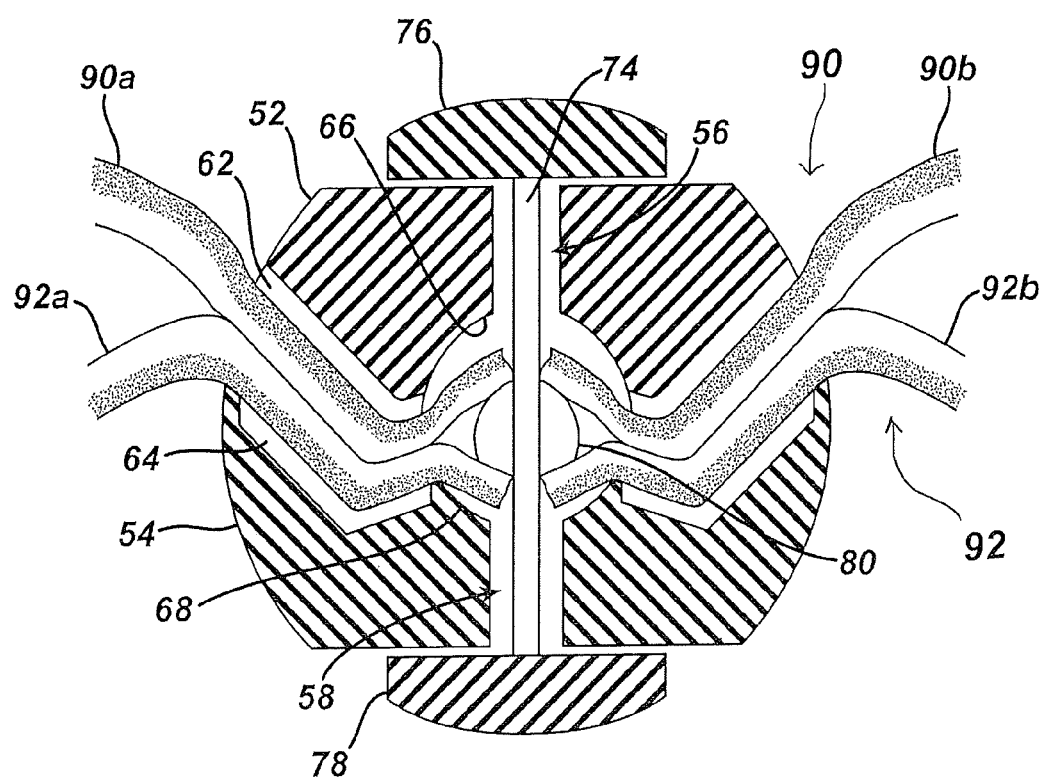
FIG. 4 depicts a cross-sectional end view of the end effector of FIG. 2, with the blade of the end effector severing tissue captured between the jaws of the end effector.

As also seen in FIGS. 2-5, electrosurgical device (10) of the present example includes an elongate member (70) that is longitudinally movable along part of the length of end effector (50). Elongate member (70) is coaxially aligned with shaft (40), extends along the length of shaft (40), and translates longitudinally within shaft (40) in the present example, though it should be understood that elongate member (70) and shaft (40) may have any other suitable relationship. Elongate member (70) includes an elongate core electrode section (72), a sharp distal blade (74), an upper flange (76), and a lower flange (78). As best seen in FIG. 4, distal blade (74) extends through slots (56, 58) of jaws (52, 54), with upper flange (76) being located above first jaw (52) and lower flange (78) being located below second jaw (54). The configuration of distal blade (74) and flanges (76, 78) provides an "I-beam" type of cross section at the distal end of elongate member (70). While flanges (76, 78) extend longitudinally only along a small portion of the length of elongate member (70) in the present example, it should be understood that flanges (76, 78) may extend longitudinally along any suitable length of elongate member (70). In addition, while flanges (76, 78) are positioned along the exterior of jaws (52, 54), flanges (76, 78) may alternatively be disposed in corresponding slots formed in jaws (52, 54). For instance, each jaw (52, 54) may define a "T"-shaped slot, with parts of distal blade (74) being disposed in one portion of each "T"-shaped slot and with flanges (76, 78) being disposed in the other portions of the "T"-shaped slots. Various other suitable configurations and relationships will be apparent to those of ordinary skill in the art in view of the teachings herein.

In the present example, distal blade (74) is sharp and passive (e.g., non-energized), though it should be understood that distal blade (74) may be energized (e.g., using RF energy, ultrasonic energy, etc.), if desired. It should also be understood that distal blade (74) may be electrically insulated from core electrode section (72). Core electrode section (72) is in communication with electrical source (96) via a conductor (not shown). As described in greater detail below, activation button (26) and controller (98) regulate the communication of power to core electrode section (72). As best seen in FIG. 3, a tapered member (80) provides a structural transition from distal blade (74) to core electrode section (72).

In some versions, either jaw (52, 54) or both of jaws (52, 54) comprise teeth (not shown) adjacent to electrode surfaces (62, 64). Such teeth may further increase the ability of jaws (52, 54) to grip tissue. Such teeth may be configured (e.g., rounded) to readily grip tissue without necessarily tearing tissue. Such teeth may also be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (52, 54). As another merely illustrative variation, either jaw (52, 54) or both of jaws (52, 54) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. Other suitable variations for jaws (52, 54) will be apparent to those of ordinary skill in the art in view of the teachings herein. In addition, while core electrode section (72) has a generally circular cross-section in the present example, it should be understood that core electrode section (72) may have any other suitable cross-sectional configuration, including but not limited to elliptical, etc. As yet another merely illustrative variation, core electrode section (72) may simply be eliminated, such that elongate member (70) is not energized with RF energy.

Figure 6:
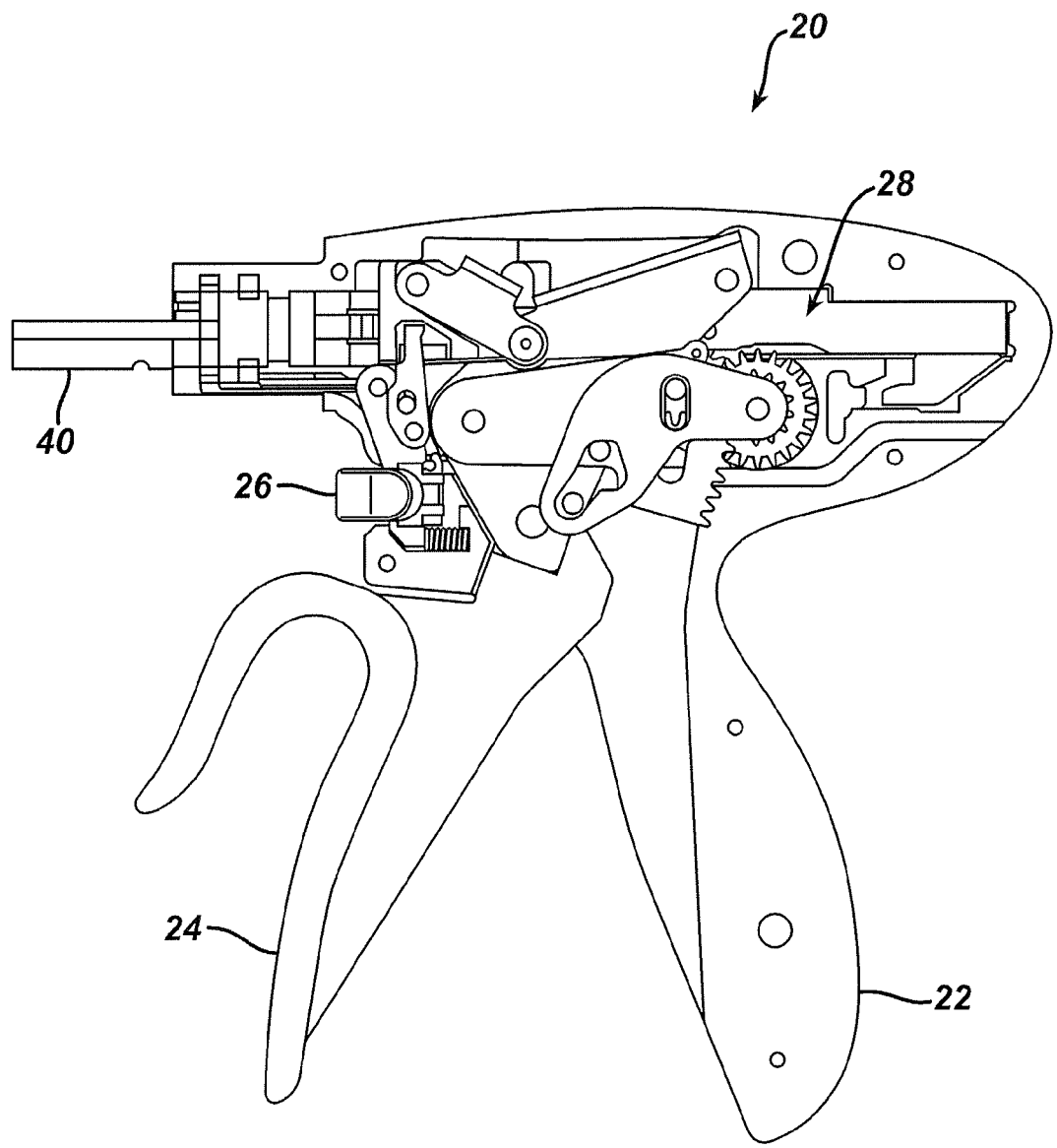
FIG. 6 depicts a side elevational view of the handle portion of the medical device of FIG. 1, with part of the handle housing removed.

As shown in FIGS. 1 and 6, handpiece (20) includes a pistol grip (22), a trigger (24), an activation button (26), and a trigger mechanism (28). Trigger (24) is pivotable relative to pistol grip (22), and is operable to simultaneously drive actuator rods (42) and elongate member (70) distally through one or more racks and pinions and other components in trigger mechanism (28). Activation button (26) is operable to selectively couple electrodes (62, 64, 72) with electrical source (96) in order to activate electrodes (62, 64, 72), as will be described in greater detail below. For instance, activation button (26) may be configured such that current does not flow between electrodes (62, 64, 72) and electrical source (96) when activation button (26) is in a non-depressed state; while current does flow between electrodes (62, 64, 72) and electrical source (96) when activation button (26) is depressed, such that activation button (26) provides a switch. Various other suitable components and features that may be provided in addition to or as an alternative to trigger (24) and activation button (26) will be apparent to those of ordinary skill in the art in view of the teachings herein.

In some versions, electrosurgical instrument (10) is configured such that elongate member (70) cannot be advanced distally until electrical current is being supplied to electrodes (62, 64, 72). By way of example only, this may be accomplished by providing a lockout against movement of trigger (24), with such a lockout requiring activation button (26) to be depressed in order for trigger (24) to move sufficiently enough to advance elongate member (70) distally. Some versions of electrosurgical instrument (10) permit electrical current to be supplied to electrodes (62, 64, 72) before elongate member (70) is advanced distally. In addition, electrosurgical instrument (10) may configured such that elongate member (70) can be advanced distally while current is simultaneously being supplied to electrodes (62, 64, 72). It should also be understood that, in some versions, trigger mechanism (28) may be constructed in accordance with at least some of the teachings of U.S. patent application Ser. No. 12/576,776, issued as U.S. Pat. No. 8,939,974 on Jan. 27, 2015.

While trigger (24) of the present example provides simultaneous distal translation of elongate member (70) and actuator rods (42), it should be understood that elongate member (70) and actuator rods (42) may be actuated independently in some other versions. It should also be understood that elongate member (70) and/or actuator rods (42) may be resiliently biased to a proximal position, such that when the user squeezes trigger (24) toward grip (22), elongate member (70) and actuator rods (42) translate distally; yet when the user then releases trigger (24), elongate member (70) and actuator rods (42) translate distally. Similarly, jaws (52, 54) may be resiliently biased to an open position. As yet another merely illustrative variation, and as noted elsewhere herein, actuator rods (42) may simply be eliminated in some versions. In some such versions, elongate member (70) is used to close jaws (52,

54). For instance, elongate member (70) may close jaws (52, 54) as elongate member (70) moves along a first range of longitudinal motion; while elongate member (70) severs tissue with distal blade (74) (as described in greater detail below) as elongate member (70) moves along a second range of longitudinal motion.

Figure 5:
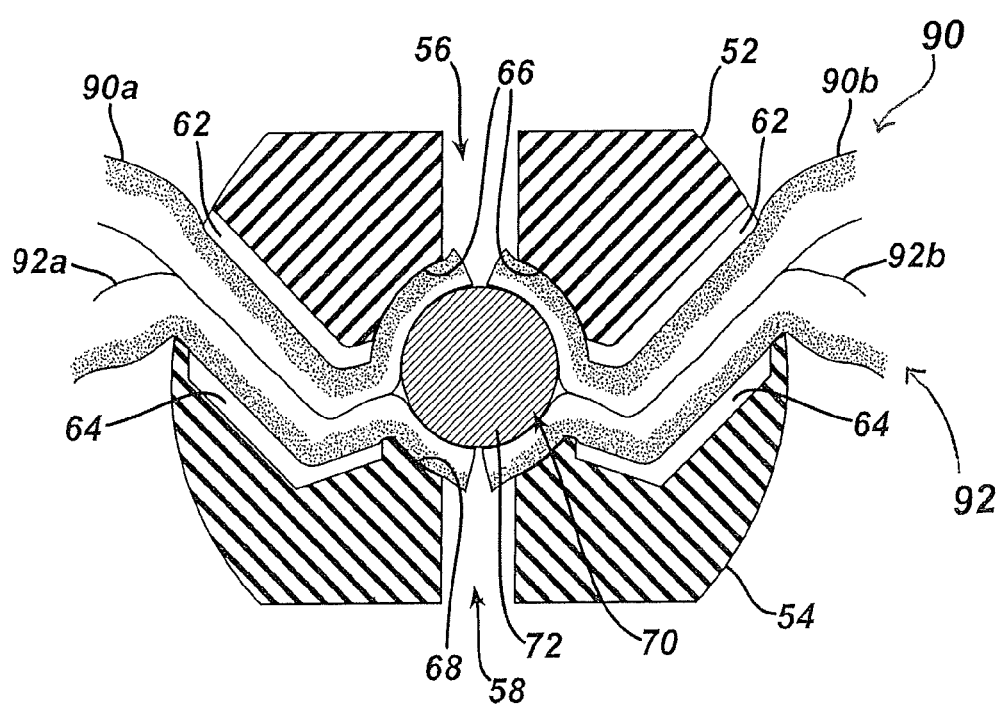
FIG. 5 depicts a cross-sectional end view of the end effector of FIG. 2, with the central electrode of the end effector contacting the severed tissue captured between the jaws of the end effector.

In an exemplary use, and as best shown in FIGS. 4-5, a first layer of tissue (90) and a second layer of tissue (92) are captured between jaws (52, 54). In particular, actuator rods (42) are actuated by squeezing trigger (24) toward pistol grip (22), to pivot first jaw (52) toward second jaw (54) to clamp down on tissue layers (90, 92). As noted above, in some versions where actuator rods (42) are eliminated, flanges (76, 78) may act to pivot first jaw (52) toward second jaw (54) instead, when elongate member (70) is actuated by squeezing trigger (24) toward pistol grip (22). In some settings, tissue layers (90, 92) are part of the same natural lumen defining anatomical structure (e.g., blood veseel, portion of gastrointestinal tract, portion of reproductive system, etc.) in a patient. For instance, first tissue layer (90) may comprise the top portion of a blood vessel while second tissue layer (92) comprises the bottom portion of the blood vessel, along the same region of length of the blood vessel (e.g., such that the fluid path through the blood vessel before use of electrosurgical device (10) is in the left-right direction in the views shown in FIGS. 4-5). In other words, the lengths of jaws (52, 54) may be oriented perpendicular to (or at least generally transverse to) the length of the blood vessel. With tissue layers (90, 92) captured between jaws (52, 54) and clamped by jaws (52, 54), elongate member (70) is advanced distally by the user squeezing trigger (24) toward pistol grip (22).

As elongate member (70) is advanced distally, distal blade (74) simultaneously severs tissue layers (90, 92), resulting in separated first layer portions (90*a*, 90*b*) being apposed with respective separated second layer portions (92*a*, 92*b*). In some versions, this results in a blood vessel being cut in a direction that is generally transverse to the length of the blood vessel. It should be understood that the presence of flanges (76, 78) immediately above and below jaws (52, 54), respectively, may help keep jaws (52, 54) in a closed and tightly clamping position. In particular, flanges (76, 78) may help maintain a significantly compressive force between jaws (52, 54). In some versions, as noted above, flanges (76, 78) alone are used as cams to close jaws (52, 54) together, such that actuating rods (42) are simply eliminated. As best seen in FIG. 5, once core electrode section (72) reaches severed layer portions (90*a*, 90*b*, 92*a*, 92*b*), core electrode section (72) compresses first layer portions (90*a*, 90*b*) against partially cylindraceous recess (66) of first jaw (52); and second layer portions (92*a*, 92*b*) against partially cylindraceous recess (68) of second jaw (54). It should be understood that the presence and configuration of tapered member (80) may facilitate the separation and compression of severed layer portions (90*a*, 90*b*, 92*a*, 92*b*) to transition from the configuration shown in FIG. 4 to the configuration shown in FIG. 5.

With severed layer portions (90*a*, 90*b*, 92*a*, 92*b*) being compressed between jaws (52, 54) and being further compressed between core electrode section (72) and partially cylindraceous recesses (66, 68), electrode surfaces (62, 64, 72) are activated with bipolar RF energy by the user depressing activation button (26). In particular, electrodes (62, 64, 72) are selectively coupled with electrical source (96) (e.g., by the user depressing button (26), etc.) such that electrode surfaces (62, 64) of jaws (52, 54) are activated with a common first polarity while electrode surface (72) of elongate member (70) is activated at a second polarity that is opposite to the first polarity. Thus, a bipolar RF current flows between electrode surface (72) of elongate member (70) and electrode surfaces (62, 64) of jaws (52, 54), through the compressed regions of severed layer portions (90*a*, 90*b*, 92*a*, 92*b*). This bipolar RF energy ultimately thermally welds tissue layer portions (90*a*, 92*a*) together and tissue layer portions (90*b*, 92*b*) together. In certain circumstances, the heat generated by activated electrode surfaces (62, 64, 72) can denature the collagen within the tissue layer portions (90*a*, 90*b*, 92*a*, 92*b*) and, in co-operation with clamping pressure provided by jaws (52, 54), the denatured collagen can form a seal within the tissue layer portions (90*a*, 90*b*, 92*a*, 92*b*). Thus, the severed ends of the natural lumen defining anatomical structure are hemostatically sealed shut, such that the severed ends will not leak bodily fluids. As noted elsewhere herein, electrode surfaces (62, 64, 72) may be activated with bipolar RF energy before elongate member (70) even begins to translate distally and thus before the tissue is even severed.

In some versions, end effector (50) includes one or more sensors (not shown) such sensors may be configured to sense a variety of parameters at end effector (50), including but not limited to temperature of adjacent tissue, electrical resistance or impedance of adjacent tissue, voltage across adjacent tissue, forces exerted on jaws (52, 54) by adjacent tissue, etc. By way of example only, end effector (50) may include one or more positive temperature coefficient (PTC) thermistors (e.g., PTC polymer, etc.). Data from such sensors may be communicated to controller (98). Controller (98) may process such data in a variety of ways. By way of example only, controller (98) may modulate or otherwise change the RF energy being delivered to electrode surfaces (62, 64, 72), based at least in part on data acquired from one or more sensors at end effector (50). In addition or in the alternative, controller (98) may alert the user to one or more conditions via an audio and/or visual feedback device (e.g., speaker, lights, display screen, etc.), based at least in part on data acquired from one or more sensors at end effector (50). It should also be understood that some kinds of sensors need not necessarily be in communication with controller (98), and may simply provide a purely localized effect at end effector (50). For instance, a PTC thermistor at end effector (50) may automatically reduce the energy delivery at electrode surfaces (62, 64, 72) as the temperature of the tissue and/or end effector (50) increases, thereby reducing the likelihood of overheating. In some such versions, a PTC thermistor element is in series with the power supply and electrode surface (62, 64, 72); and the PTC thermistor provides an increased impedance (reducing flow of current) in response to temperatures exceeding a threshold. Furthermore, it should be understood that electrode surfaces (62, 64, 72) may be used as sensors (e.g., to sense tissue impedance, etc.). Various kinds of sensors that may be incorporated into electrosurgical device (10) will be apparent to those of ordinary skill in the art in view of the teachings herein. Similarly various things that can be done with data from sensors, by controller (98) or otherwise, will be apparent to those of ordinary skill in the art in view of the teachings herein.

It should also be understood that end effector (50) may include one or more tissue cooling features (not shown) that reduce the degree or extent of thermal spread caused by end effector (50) on adjacent tissue when electrode surfaces (62, 64, 72) are activated. Various suitable forms that such cooling features may take will be apparent to those of ordinary skill in the art in view of the teachings herein.

As yet another merely illustrative variation, core electrode surface (72) may be eliminated such that elongate member (70) simply comprises blade (74) and flanges (76, 78) at the distal end of an electrically passive translating rod, beam, or other type of elongate member. In some such versions, RF energy is delivered to first electrode surface (62) at a first polarity and to second electrode surface (64) at a second (opposite) polarity, such that the RF current flows between electrode surfaces (62, 64) through severed layer portions (90a, 90b, 92a, 92b). Still other suitable features, components, configurations, variations, and operabilities that may be incorporated into electrosurgical device (10) will be apparent to those of ordinary skill in the art in view of the teachings herein.

While several of the teachings below are described as variations to electrosurgical device (10), it should be understood that various teachings below may also be incorporated into various other types of devices. By way of example only, in addition to being readily incorporated into medical device (10), various teachings below may be readily incorporated into the devices taught in U.S. Pat. No. 7,416,101; U.S. Pat. No. 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0209990, issued as U.S. Pat. No. 8,657,174 on Feb. 25, 2014; U.S. Pub. No. 2010/0069940, issued as U.S. Pat. No. 9,023,071 on May 5, 2015; and/or U.S. Provisional Application Ser. No. 61/410,603, amongvarious other devices. Other suitable devices into which the following teachings may be incorporated will be apparent to those of ordinary skill in the art in view of the teachings herein.

II. EXEMPLARY INCORPORATION OF MOTOR TO DRIVE MOVABLE COMPONENT OF ELECTROSURGICAL DEVICE

As noted above, elongate member (70) in electrosurgical device (10) is manually driven by squeezing trigger (24) toward grip (26) to actuate manual trigger mechanism (28) through purely/exclusively mechanical force transfers. In some instances, it may be desirable to use a motor or some other device to drive elongate member (70). This may reduce the manual force required to squeeze trigger (24), which may significantly increase usability in instances such as those where the user has relatively weak gripping strength, electrosurgical device (10) is being used in a relatively long procedure where surgeon fatigue may become a factor, and/or when relatively tough or dense tissue is involved. Several examples below discuss various ways in which the driving of a movable feature like elongate member (70) (and movable features like jaws (52, 54), etc.) is provided by a motor or other electrically activated device, rather than being provided solely by purely/exclusively manual mechanical actuation. In the below examples, the electrosurgical devices lack an equivalent to actuator rods (42). Instead, the equivalent to elongate member (70) cams against the equivalents to jaws (52, 54) to close jaws (52, 54), though it should be understood that some equivalent to actuator rods (42) may be used if desired; or jaws (52, 54) may be closed in some other fashion.

Figure 7:
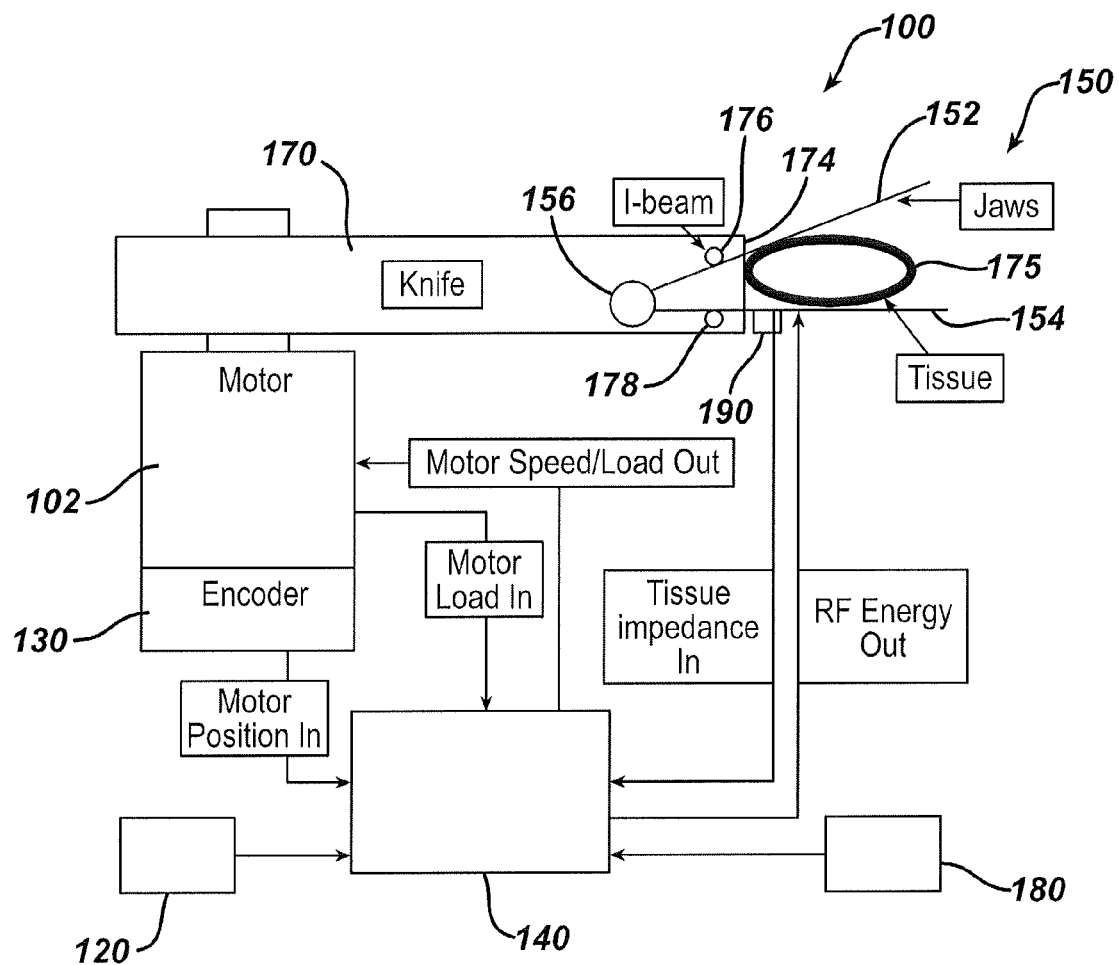
FIG. 7 depicts a schematic diagram of an exemplary electrosurgical device including a motor and feedback based control.

FIG. 7 shows a schematic view of an exemplary electrosurgical device (100) that includes a motor (102). Motor (102) may comprise an AC motor or DC motor of any suitable type, including but not limited to a stepper motor. Electrosurgical device (100) also includes jaws (152, 154) similar to jaws (52, 54) above; and an elongate member (170) similar to elongate member (70) above. Upper jaw (152) pivots toward and away from lower jaw (154), about pivot (156). Elongate member (170) of this example further includes a sharp distal blade (174), an upper transverse flange (176), and a lower transverse flange (178). Flanges (176, 178) cam against the outer surfaces of jaws (152, 154) to make jaws (152, 154) clamp down on tissue (175) as elongate member (170) is advanced distally; while distal blade (174) severs the clamped tissue (175) as elongate member (170) is advanced distally. Motor (102) is operable to drive elongate member (170) distally. Various suitable ways in which a motor (102) may be used to drive an elongate member (170) distally will be described in greater detail below, while still other suitable ways will be apparent to those of ordinary skill in the art in view of the teachings herein. In the present example, elongate member (170) is electrically passive and does not include a core electrode that is similar to core electrode (72) described above. Instead, jaws (152, 154) present bi-polar RF electrodes with opposing polarities. In some other versions, however, elongate member (170) may have a core electrode with a polarity that is opposite to a polarity that is common among electrodes of jaws (152, 154).

Electrosurgical device (100) of the present example further includes a user input feature (120), an encoder (130), a control module (140), a power source (180), and a sensor (190). Control module (140) serves as an operational hub for various components of electrosurgical device, as will be described in greater detail below. In particular, control module (140) is in communication with motor (102), user input feature (120), encoder (130), power source (180), and sensor (190). Control module (140) may include a variety of components, including but not limited to one or more printed circuit boards, one or more memory devices, one or more microprocessors, etc. Other suitable components that may be included in control module (140) will be apparent to those of ordinary skill in the art in view of the teachings herein.

User input feature (120) may comprise a button, a trigger (e.g., similar to trigger (24), above, etc.), and/or any other suitable type of user input feature. In some versions, control module (140) is operable to activate motor (102) to fully advance elongate member (170) to clamp and sever tissue (175) and simultaneously activate electrodes in jaws (152, 154) as soon as the user actuates user input feature (120). In some other versions, control module (140) just activates motor (102) enough to advance elongate member (170) far enough just to close jaws (152, 154) to clamp tissue (175) when the user actuates user input feature (120). In some such versions, control module (140) waits for the user to actuate user input feature (120) a second time before control module (140) activates motor (102) to continue advancing motor elongate member (170) to sever clamped tissue (175) and simultaneously activate electrodes in jaws (152, 154). In some other versions, control module (140) waits for data from sensor (190) and/or other variables in a control algorithm to indicate the appropriate time/circumstances to activate motor (102) to continue advancing motor elongate member (170) to sever clamped tissue (175) and simultaneously activate electrodes in jaws (152, 154). While some exemplary control algorithms will be described in greater detail below, other suitable variables and associated values/ranges that may be used to form control algorithms will be apparent to those of ordinary skill in the art in view of the teachings herein.

Encoder (130) of the present example comprises a conventional encoder assembly that is configured to track operation of motor (102). By way of example only, encoder (130) may include a wheel with slots, tabs, and/or other optically trackable features. Such a wheel may be fixedly mounted to a drive shaft of motor (102), such that the wheel rotates unitarily with the drive shaft of motor (102). Encoder (130) may further include an optical sensor that is fixedly positioned within electrosurgical device (100) and that is operable to monitor movement of the wheel. Thus, as shown in FIG. 7, encoder (130) may provide data to control module (140) indicating the rotational position of the drive shaft of motor (102), the rate of rotation of the drive shaft of motor (102), the number of rotations of the drive shaft of motor (102), etc. Such data may be interpreted and processed as being further representative of the longitudinal position of elongate member (170), the rotational position of jaw (152) relative to jaw (154), etc. By way of example only, in some versions data from encoder (130) (taken at the time when data from sensor (190) indicates that both jaws (152, 154) have contacted tissue) is interpreted by control module (140) to represent the thickness of tissue (175) between jaws (152, 154). Examples of how such tissue thickness data may be used will be described in greater detail below. It should also be understood that control module (140) may alert the user of the device or prevent continued clamping of jaws (152, 154) when data from encoder (130) and/or other sources indicates that tissue (175) is too thick for electrosurgical device (100) to handle. Of course, as with various other components referred to herein, encoder (130) is merely optional.

Power source (180) of the present example comprises one or more batteries, capacitors, supercapacitors, and/or other types of power sources integral with electrosurgical device (100). For instance, to the extent that electrosurgical device (100) includes a handpiece or handheld housing/body, power source (180) may be located within such a handpiece or handheld housing/body. It should therefore be understood that all of the components of electrosurgical device (100) shown in FIG. 7 may be integrated into a single, self-contained, handheld unit. In some other versions, power source (180) comprises a conventional wall outlet and/or a piece of capital equipment, such that electrosurgical device (100) is externally tethered to power source (180). Similarly, it should be understood that control module (140) may be located within a handpiece or handheld housing/body of electrosurgical device (100); or be provided in a separate piece of capital equipment, tethered with electrosurgical device (100) via one or more cables, etc. In some such versions, power source (180) and control module (140) may be integrated together in a single piece of capital equipment that is tethered externally to electrosurgical device (100).

Sensor (190) may take numerous forms. For instance, while it is shown schematically in FIG. 7 as being a separate component, sensor (190) of the present example is simply formed by the same electrodes of jaws (152, 154) that are used to deliver bipolar RF energy to tissue (175). Sensor (190) in this example is used to measure the impedance of tissue (175) and communicate the same back to control module (140). For instance, control module (140) may send a dedicated electrical pulse through the electrodes of jaws (152, 154) to measure the impedance of the tissue. Of course, various other kinds of data may be communicated back to control module (140), from one or more sensors (190) at end effector (150) or otherwise. Other types of parameters that may be sensed by one or more sensors (190) at end effector (150) will be apparent to those of ordinary skill in the art in view of the teachings herein.

As shown in FIG. 7, control module (140) processes a variety of inputs and outputs in electrosurgical device (100). In particular, and as noted above, control module (140) receives user input from user input feature (120), position data from encoder (130), and tissue impedance data from sensor (190). In addition, control module (140) receives data from motor (102) indicating the load on motor (102). The load on motor (102) may be sensed by monitoring the current consumed by motor (102), by monitoring the back electromotive force (EMF) communicated by motor (102), by monitoring changes in voltage or capacitance associated with motor (102), and/or in any other suitable fashion. In some versions, the load on motor (102) is simply not monitored. In addition to receiving the above-noted inputs, control module (140) is operable to provide two key outputs. In particular, control module (140) is operable to provide power to motor (102) to activate motor (102), to thereby drive elongate member (170) distally for closing jaws (152, 154) and cutting tissue (175); and to provide power to jaws (152, 154) to activate the electrodes of jaws (152, 154), to thereby weld and coagulate severed tissue using bipolar RF current. Control module (140) may include various types of control algorithms to vary such outputs based on the inputs. For instance, tissue impedance data from sensor (190) may be used not only to influence the power provided to the electrodes of jaws (152, 154), but also to influence the power provided to motor (102). Merely illustrative examples of motor (102) control based on tissue impedance will be described in greater detail below. Similarly, data representing the load on motor (102) may be used to influence the power provided to motor (102) and/or the RF power provided to the electrodes of jaws (152, 154). Still other various functions that may be performed by control module (140) will be apparent to those of ordinary skill in the art in view of the teachings herein.

Figure 8:
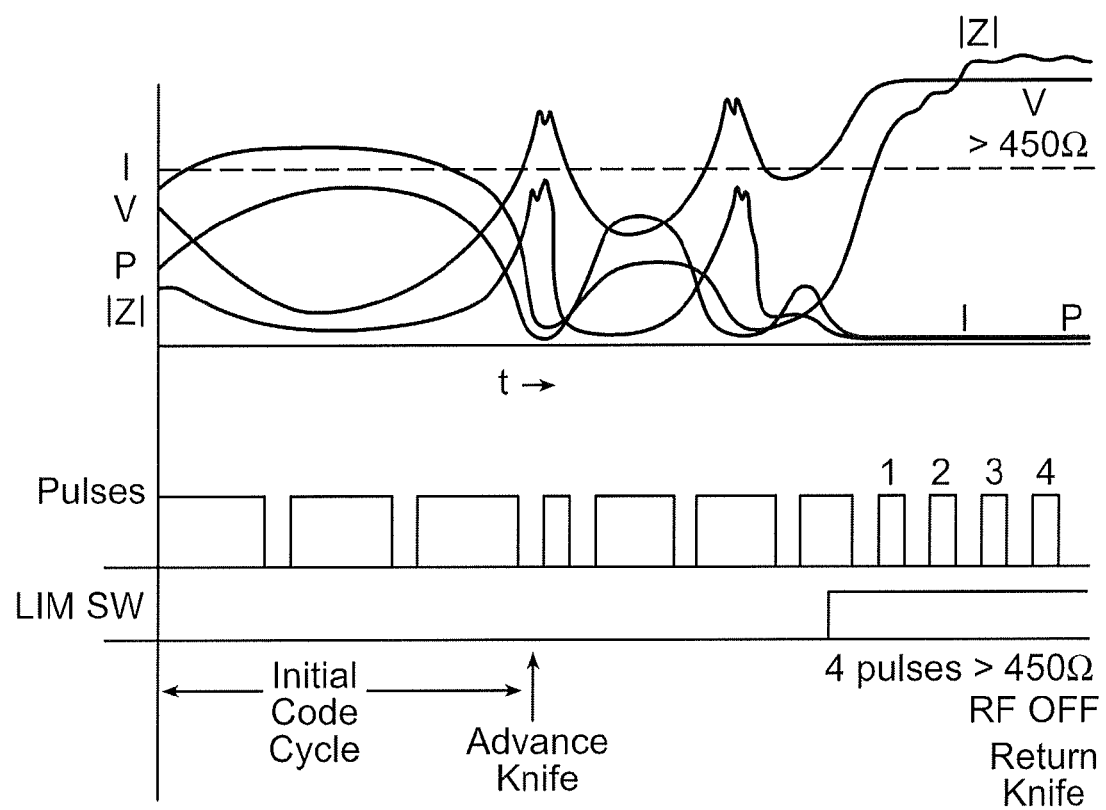
FIG. 8 depicts a graph showing exemplary relationships between various feedback and control signals during operation of the electrosurgical device of FIG. 7.

FIG. 8 shows exemplary relationships between various feedback and control signals during operation of electrosurgical device (100), which may form part of a control algorithm executed by control module (140). In particular, FIG. 8 shows, from the top portion of the graph going down, current (I) at the electrodes of jaws (152, 154), voltage (V) at the electrodes of jaws (152, 154), power (P) at the electrodes of jaws (152, 154), impedance (Z) at the electrodes of jaws (152, 154), the delivery of power (Pulses) to the electrodes of jaws (152, 154), and a control signal (LIM SW) to a limit switch. As can be seen in FIG. 8, the delivery of energy to the electrodes of jaws (152, 154) is pulsed in the present example. As will be described in greater detail below, when the impedance increases dramatically in any pulse, then the following pulse is shortened.

The initial portions of the curves in the graph of FIG. 8 depict three pulses. During the initial stage of operation, jaws (152, 154) are clamped on tissue but a knife at the distal end of elongate member (170) is not yet in contact with the tissue. As the cycle approaches the third pulse, the voltage (V) and impedance (Z) increase; while the power (P) and current (I) decrease. In the third pulse, the impedance (I) begins to increase rapidly, which results in shortening of the fourth pulse. The rapid increase in impedance (I) indicates that the tissue immediately in front of the knife has been treated and the knife should be advanced through such tissue. In some settings, this occurs at about the point when the tissue gives way to the pressure of a knife that is being linearly driven by elongate member (170). At such a stage, the tissue immediately in front to the knife may have been treated but the more distal portion of the tissue may have not yet received an adequate amount of heat energy. So as the knife is advanced there may be significant variability in the duration of the pulses, such that the behavior of electrosurgical device may be unique each time electrosurgical device (100) is used. With the initiation of the shortened fourth pulse, the knife is advanced distally by elongate member (170) in a controlled predetermined manner by motor (102). When the knife has traveled the full cutting stroke, a limit switch is closed, as shown in the (LIM SW) curve of the graph of FIG. 8. At this point, control module (140) delivers short termination pulses. When a sequence of four termination pulses in a row are received and an upper impedance (I) threshold has been crossed, control module (140) delivers a "done" alarm to the surgeon, indicating that the cutting and sealing procedure is complete, and the knife is retracted proximally to its initial position. In some other versions, electrodes at jaws (152, 154) continue to be activated at this stage until a predetermined time (e.g., 15 seconds, etc.) has passed. In either case, control module (140) may automatically stop delivering power to electrodes at jaws (152, 154) when the "done" alarm is communicated to the surgeon.

In some instances, it may be desirable to weld and/or seal tissue without necessarily cutting the tissue; or to at least clamp and heat the tissue to some degree before cutting the tissue. By way of example only, this may be desirable in some settings where the tissue is particularly thick or dense, where electrosurgical device (100) might otherwise have difficulty simultaneously clamping and cutting the tissue. To that end, another variation of electrosurgical device (100) provides closing of jaws (152, 154) and cutting with blade (174) in separate operational stages. For instance, electrosurgical device may provide independent movement of jaw (152) and elongate member (170), such as by having a pair of actuator rods (e.g., similar to actuator rods (42)), an external closure sleeve or collar that slides along at least part of the end effector (150), etc. Such a jaw closure feature may be selectively activated manually, by motor (102), by a separate motor, or otherwise. Alternatively, elongate member (170) may be movable within two stages—a first stage or range of motion where elongate member (170) merely closes jaws (152, 154) without yet cutting tissue within jaws (152, 154) and a second stage or range of motion where elongate member (170) cuts tissue clamped within jaws (152, 154). In either case, electrodes in jaws (152, 154) may be activated as jaws (152, 154) are closed on the tissue, without the tissue being cut yet. As the activated electrodes heat the tissue, the tissue may eventually become relatively easier to cut, such that elongate member (170) may then be used to cut the tissue after the tissue has been clamped and heated/sealed by jaws (152, 154) for some period of time. An actuator for jaws (152, 154) may even be reciprocated at any stage in this process, resulting in the jaws (152, 154) "chewing" on the tissue to further soften it up and/or to make it more susceptible to heating/sealing and/or cutting.

It should also be understood that, in versions where motor (102) is used to close jaws (152, 154), the load on motor (102) may be monitored by control module (140), which may slow motor (102) or otherwise change power delivery to motor (102) based on the load on motor (102). Control module (140) may also regulate the power delivered to motor (102) based at least in part on parameters of the tissue itself (e.g., temperature, impedance, etc.), as sensed by sensor (190). In determining when to advance elongate member (170) through a range of motion to sever tissue, control module (140) may monitor the load on motor (102) as jaws (152, 154) are clamping on the tissue and/or monitor parameters of the tissue itself (e.g., temperature, impedance, etc.), such as using sensor (190).

As another merely illustrative example of operation, a relatively thick piece of vascular tissue may be placed between jaws (152, 154). Motor (102) is activated to close jaws (152, 154) on the tissue until control module (140) detects a load (e.g., by power increase, voltage change, capacitance change, etc.), representing the presence of tissue between jaws (152, 154). At that point, control module (140) sends an electrical pulse through the electrodes of jaws (152, 154) to sense the impedance of the tissue between jaws (152, 154). Control module (140) also receives data from encoder (130) or elsewhere to indicate how far jaws (152, 154) have closed. At this point, control module (140) "knows" how thick the tissue is (based on degree of jaw (152, 154) closure) and what the impedance is of the tissue. With this knowledge, control module (140) adjusts the speed of motor (102), other operational parameters of motor (102), and/or the RF energy delivered to the electrodes of jaws (152, 154).

For instance, when relatively thick tissue is sensed and/or when the impedance of the tissue is relatively low, control module (140) may initially provide a relatively slow motor (102) speed and relatively high RF energy, or vice versa, in order to get started working on the thick tissue. In some instances, reducing the motor (102) speed in response to relatively thick tissue may ultimately lead to a better tissue seal and/or less mechanical trauma to the tissue. In addition or in the alternative, motor (102) may be repeatedly activated in forward and reverse in short bursts in response to relatively thick tissue and/or when the impedance of the tissue is relatively low (e.g., liver tissue or lung tissue, etc.), resulting in the jaws (152, 154) "chewing" on the tissue to further soften it up and/or to make it more susceptible to heating/sealing and/or cutting. In either or both scenarios, as jaws (152, 154) continue to compress and heat/seal the tissue, control module (140) may continue to monitor parameters such as tissue impedance, load on motor (102), thickness of the tissue, etc., as part of a feedback loop. As the tissue impedance increases and/or the load decreases, control module (140) speeds up motor (102) to speed compression and control module (140) also reduces the RF delivered to the electrodes of jaws (152, 154). A similar control algorithm may be followed when relatively thin tissue is involved, though it should be understood that control module (140) may speed up the whole process when it recognizes that the tissue is thin. It should also be understood that the above control algorithms could be based on other factors such as tissue density and/or other tissue properties, not necessarily being based on tissue thickness and/or impedance, etc. It should also be understood that a control algorithm may comprise a function of just one variable or a function of a combination of variables.

Furthermore, in versions where the completion of a drive stroke of elongate member (170) and/or the activation of electrodes in jaws (152, 154) is contingent on certain circumstances per a control algorithm executed by control module (140), electrosurgical device (100) may further include a user feedback feature to provide an indication to the user representing the operational state of elongate member (170) and/or electrodes in jaws (152, 154). For instance, electrosurgical device (100) may include one or more lights, a beeping feature, and/or a graphical rendering to show the user when cutting with blade (174) is complete, when tissue has been sealed by electrodes in jaws (152, 154), and/or when some other operational stage has been reached. This may reduce the likelihood that the user pulls end effector (150) away from tissue at the surgical site prematurely.

While the following examples include motors and solenoids to drive a movable component of an electrosurgical device, it should be understood that various other types of components and devices may be used to drive a movable component of an electrosurgical device. Additional examples include, but are not limited to, pneumatic actuators, hydraulic actuators, electro-active polymers, ultrasonic motors, etc. It should be understood that these alternatives may be readily incorporated into the examples below, as a substitute for or supplement for a motor and/or solenoid.

While the foregoing describes exemplary electrosurgical device (100) in general or conceptual terms, the following teachings provide additional details on merely illustrative examples of how several features of electrosurgical device (100) may be carried out in practice. Of course, it is contemplated that various teachings herein may be combined in numerous ways, and it should be understood that none of the teachings herein are intended to represent the limits of the inventors' contemplation. Various other examples of how several features of electrosurgical device (100) may be carried out in practice will be apparent to those of ordinary skill in the art in view of the teachings herein, and those examples are well within the inventors' contemplation.

A. Exemplary Rack and Pinion Driver

Figure 9:
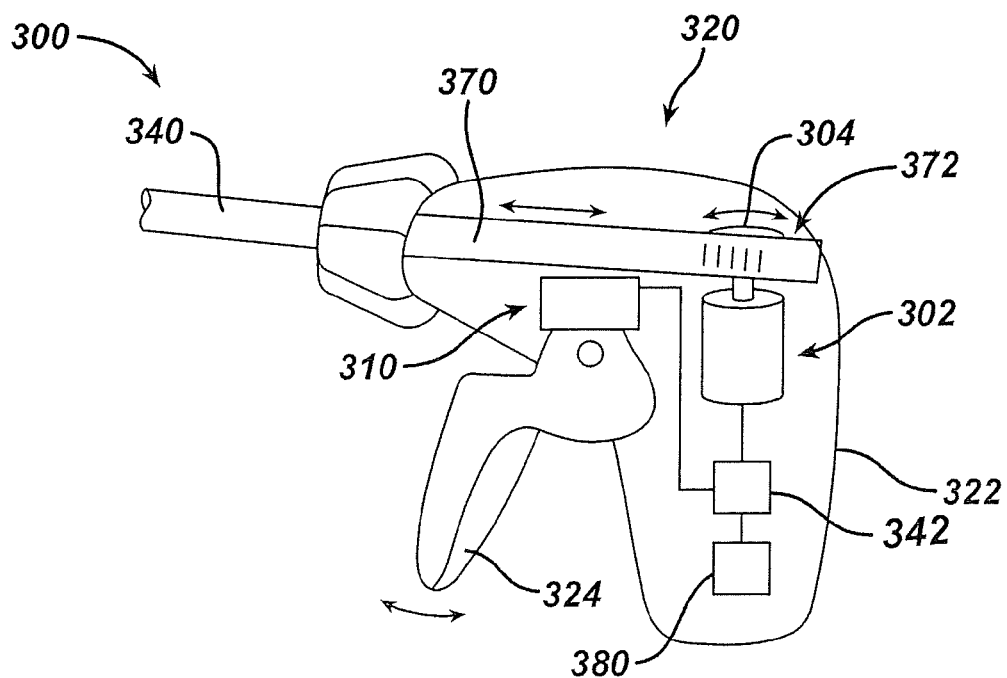
FIG. 9 depicts a partial view of an exemplary electrosurgical device including a motor driven blade.
Figure 10:
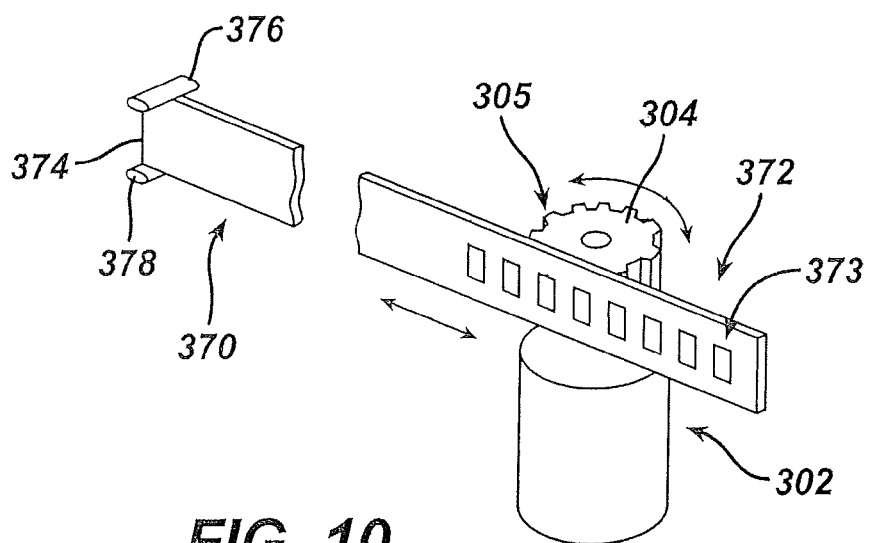
FIG. 10 depicts a partial view of the rack and pinion drive of the electrosurgical device of FIG. 9.

FIG. 9 depicts an exemplary electrosurgical device (300) comprising a handpiece (320), a shaft (340) extending distally from handpiece (320), and an elongate member (370) slidably disposed in shaft (340). Handpiece (320) includes a pistol grip (322) and a trigger (324). An end effector (not shown), similar to end effectors (50, 150) described elsewhere herein, is disposed at the distal end of shaft (340), and includes a pair of jaws with integral electrodes. Elongate member (370) is similar to elongate member (170) described above. In particular, and as shown in FIG. 10, elongate member (370) has a blade (374) and pair of flanges (376, 378) at its distal end. Elongate member (370) is movable distally to close the jaws at the end effector and sever tissue clamped between the jaws. A motor (302) is located within handpiece (320). Motor (302) includes an integral drive pinion (304), such that motor (302) is operable to rotate drive pinion (304). The proximal portion of elongate member (370) includes a rack (372) engaged with drive pinion (304). In particular, rack (372) includes a plurality of slots (373), with teeth (305) of drive pinion (304) being disposed in slots (373). Alternatively, rack (372) may include teeth that mesh with teeth (305) of drive pinion (304). It should be understood that, as drive pinion (304) is rotated by motor (302), elongate member (370) translates longitudinally due to engagement between drive pinion (304) and rack (372).

As also shown in FIG. 9, electrosurgical device (300) includes a trigger movement sensor (310), a control module (342), and a power source (380). Trigger movement sensor (310) of the present example is in communication with trigger (324), such that trigger movement sensor (310) senses movement of trigger (324) toward and away from grip (322). By way of example only, trigger movement sensor (310) may comprise a proximity sensor, an encoder, a hall effect sensor, a rheostat, etc. Other suitable forms that trigger movement sensor (310) may take will be apparent to those of ordinary skill in the art in view of the teachings herein. Trigger movement sensor (310) is also in communication with control module (342), which activates motor (302), activates electrodes in the jaws of the end effector, initiates a control algorithm, and/or otherwise reacts in response to movement of trigger (324) as sensed by and communicated from trigger movement sensor (310). Thus, trigger (324) and trigger movement sensor (310) may together function similar to user input feature (120) referenced above. Furthermore, control module (342) may account for different positions of trigger (324) relative to grip (322) to influence a control algorithm, beyond simply detecting whether trigger (324) is being squeezed or not. For instance, when trigger (324) is only partially squeezed, control module (342) may simply clamp the jaws at the end effector without cutting the clamped tissue until trigger (324) is fully squeezed. A detent feature or other feature may provide tactile feedback to the surgeon via trigger (324) to indicate transitions between such stages of actuation. Other suitable ways in which control module (342) may account for partial actuations of trigger (324) will be apparent to those of ordinary skill in the art in view of the teachings herein.

It should be understood that, by incorporating trigger movement sensor (310) and using motor (302), the grip of the surgeon's hand no longer directly provides power to the jaws or blade at end effector. In other words, trigger (324) is taken out of the mechanical part of the drive train, and instead serves as a more easily actuated electromechanical component. Electrosurgical device (300) may therefore be relatively easier to operate than electrosurgical device (10), due to the absence of a purely mechanical drive train like trigger mechanism (28) of electrosurgical device (10). Of course, trigger (324) may take a variety of alternative forms, including but not limited to a button, slider, etc.

Other aspects of control module (342) and power source (380) may be provided in a manner similar to that described above with respect to control module (140) and power source (180). By way of example only, control module (342) may execute various control algorithms as described herein; and control module (342) and/or power source (380) may be integrated within handpiece (320) or may be external to handpiece (320). Similarly, other teachings herein relating to electrosurgical devices (10, 100) may be readily incorporated into electrosurgical device (300); and vice versa.

B. Exemplary Solenoid Driver

Figure 11:
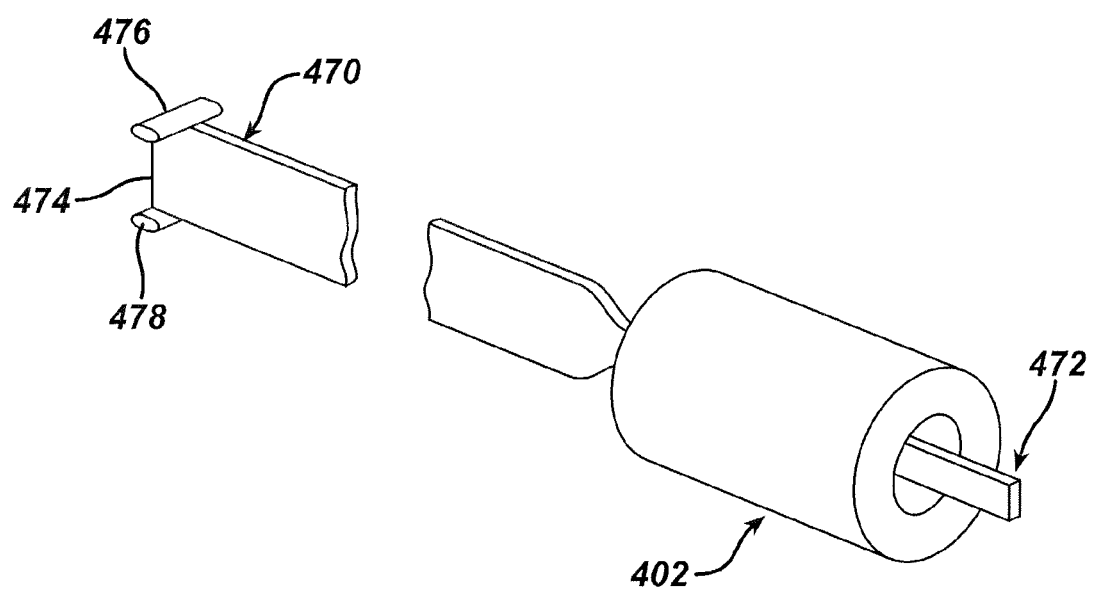
FIG. 11 depicts a partial view of an exemplary solenoid driven blade that may be used in the electrosurgical device of FIG. 9.

FIG. 11 depicts components that may be used in place of elongate member (370), motor (302), and pinion (304). In particular, FIG. 11 shows a solenoid assembly (402) that may be used to drive an elongate member (470). Elongate member (470) of this example includes a sharp blade (474) and flanges (476, 478), much like other elongate members (70, 170, 370) referred to herein. However, the proximal portion of elongate member (470) defines a core element (472) of solenoid assembly (402). It should therefore be understood that selective activation of solenoid assembly (402), by a control module or otherwise, may longitudinally translate elongate member (370). Of course, elongate member (470) and solenoid assembly (402) may be readily incorporated into any electrosurgical device (10, 100, 300) referred to herein.

C. Exemplary Lead Screw Driver

Figure 12:
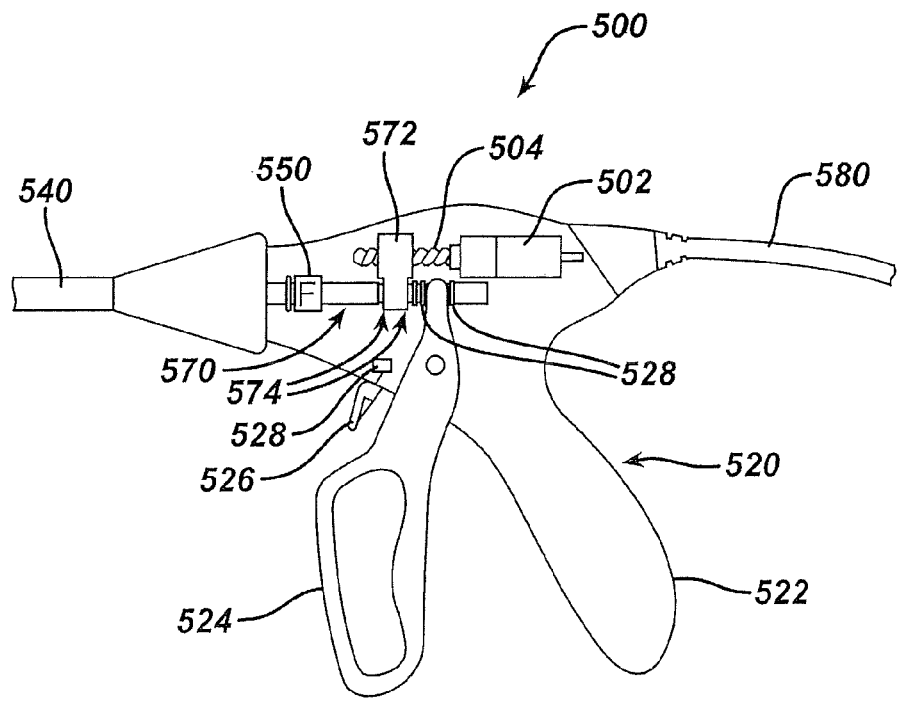
FIG. 12 depicts a partial view of an exemplary electrosurgical device including a motor driven blade and a force transducer.

FIG. 12 depicts another exemplary electrosurgical device (500), comprising a handpiece (520), a shaft (540) extending distally from handpiece (520), and an elongate member (570) slidably disposed in shaft (540). Handpiece (520) includes a pistol grip (522), a trigger (524), and a button (526). An end effector (not shown), similar to end effectors (50, 150) described elsewhere herein, is disposed at the distal end of shaft (540), and includes a pair of jaws with integral electrodes. Elongate member (570) is similar to elongate member (170) described above. In particular, elongate member (570) has a blade (not shown) and pair of flanges (not shown) at its distal end. Elongate member (570) is movable distally to close the jaws at the end effector and sever tissue clamped between the jaws. A motor (502) is located within handpiece (520), and includes an encoder (not shown) like encoder (130) described above. Motor (502) is shown as being coupled with a cable (580), which is further coupled with a combined control module and power source (not shown), though it should be understood that a control module and/or power source may be integrated within handpiece (520) if desired. A lead screw (504) extends distally from motor (502) and is rotatable by motor (502) to drive elongate member (570) as described in greater detail below.

A force transducer (550) or load cell is engaged with elongate member (570), positioned in-line with elongate member (570), and is configured to sense a force load encountered by elongate member (570) during operation of electrosurgical device (500). Data from force transducer (550) may be communicated to the remote control module via cable (580) and/ or be communicated to a control module within handpiece (520). It should be understood that data force transducer (550) may be used as part of a control algorithm, influencing delivery of power to motor (502) and/or influencing delivery of RF energy to electrodes at the end effector at the distal end of shaft (540). It should also be understood that a force load encountered by elongate member (570) may be detected in various other ways, including but not limited to monitoring loads on motor (502).

A nut (572) is also engaged with elongate member (570) and with lead screw (504). In particular, as motor (502) is activated to rotate lead screw (504), lead screw (504) drives nut (572) longitudinally, which in turn drives elongate member (570) longitudinally. However, there is some degree of lost motion provided by longitudinal clearance (574) between elongate member (570) and nut (572), such that elongate member (570) is longitudinally movable relative to nut (572) through a certain range of motion. Such lost motion may be provided in various ways. For instance, nut (572) may be seated on elongate member (570) between a pair of flanges, with such flanges being separated by a distance that is greater than the length of nut (572) along elongate member (570). As another merely illustrative example, nut may be seated on elongate member (570) in a cylindraceous recess, with such a recess having a length that is greater than the length of nut (572) along elongate member (570). Other suitable ways in which lost motion may be provided will be apparent to those of ordinary skill in the art in view of the teachings herein.

Providing lost motion between elongate member (570) and nut (572) may permit elongate member (570) to be translated manually along one range of motion and electromechanically along another range of motion. In particular, the lost motion configuration of the present example allows the user to manually translate elongate member (570) distally enough to close the jaws of the end effector at the end of shaft (570) by squeezing trigger (524) toward grip (522). However, the lost motion configuration is further configured such that nut (572) arrests further manual distal movement of elongate member (570) after the jaws are closed, such that elongate member (570) cannot be driven any further to sever tissue clamped between the jaws. In order to sever tissue clamped between the jaws in the present example, the user must press button (526) while simultaneously squeezing trigger (524) toward grip (522). These combined inputs at trigger (524) and button (526) will activate motor (502) to rotate lead screw (504), thereby advancing elongate member (570) distally to sever the clamped tissue. Button (526) and trigger (524) may thus include sensors (528) operable to detect actuation of button (526) and trigger (524), such that the same may be communicated to a control module.

In some settings, a user may wish to just use electrosurgical device (500) as a simple tissue grasper and/or to perform blunt dissection. To that end, the user may simply squeeze trigger (524) toward grip (522) to close the jaws at the end effector, without pressing button (526). While this will advance elongate member (570) far enough to close the jaws, it will not advance elongate member (570) far enough to cut tissue clamped between the jaws. Thus, in the absence of button (526) being pressed in this example, none of the electrical or electromechanical components are actuated yet.

Similarly, a user may wish to simply clamp and seal or weld tissue without yet cutting the tissue. To that end, electrosurgical device (500) may be configured such that the user may first squeeze trigger (524) toward grip (522) to manually clamp tissue with jaws at the end effector; then press button (526) to activate delivery of RF energy to the tissue through electrodes in the jaws at the end effector. At this stage, the motor (502) may remain inactive despite trigger (524) and button (526) being actuated simultaneously, such that elongate member (570) is not yet advance distally far enough to sever the tissue clamped between the jaws. In some versions, electrosurgical device (500) relies on feedback (e.g., force loads, tissue impedance, tissue thickness, etc.) in executing a control algorithm at this stage, to determine the appropriate time for cutting of tissue, and to automatically advance elongate member (570) to sever tissue at the appropriate time and at the appropriate speed/force. In some other versions, electrosurgical device (500) simply waits for the user to release button (526) and re-press button (526) while still squeezing trigger (524), and electrosurgical device (500) then activates motor (502) to advance elongate member (570) further to sever tissue. As yet another merely illustrative variation, another button (not shown) may be provided for selectively activating motor (502) to advance elongate member (570) to sever tissue after the tissue has been manually clamped using trigger (524). Such an additional button may be rendered inoperable unless and until button (526) is being depressed; and may just initiate a feedback-based control algorithm to advance elongate member (570) rather than necessarily immediately advancing elongate member (570). In any of the above examples, elongate member (570) may be retracted by motor (502) when trigger (524) is released, when button (526) is released, and/or in response to various other conditions.

III. EXEMPLARY INCORPORATION OF TACTILE FEEDBACK IN MOTOR DRIVEN ELECTROSURGICAL DEVICE

In some settings where a mechanical actuation of a user input feature is electromechanically converted to movement of a movable component of the same device, it may be difficult for the user to tell how much force is being exerted by or encountered by the movable component. This may be particularly so when the movable component is electromechanically moved with significantly greater force then the force exerted by the user on the user input feature. The issue may be further exacerbated in situations where a person may be historically used to operating manually actuated versions of the same device, such that the person intuitively expects a certain degree of mechanical resistance by the user input feature and/or some proportional relationship between the force exerted on the user input feature and the force exerted by the associated movable component. It may therefore be desirable in certain situations to provide some degree of tactile feedback to the user of an electromechanically actuated device, to represent forces exerted by and/or encountered by one or more electromechanically actuated components of the device in real time. Several examples of such tactile feedback will be provided in greater detail below, while still further examples will be apparent to those of ordinary skill in the art in view of the teachings herein. It should also be understood that, while the following examples are provided in the context of electrosurgical devices, at least some of the following teachings may be readily applied to various other devices that include an electromechanically actuated movable member—not just electrosurgical devices.

A. Exemplary Clutch Mechanism on Trigger

Figure 13:
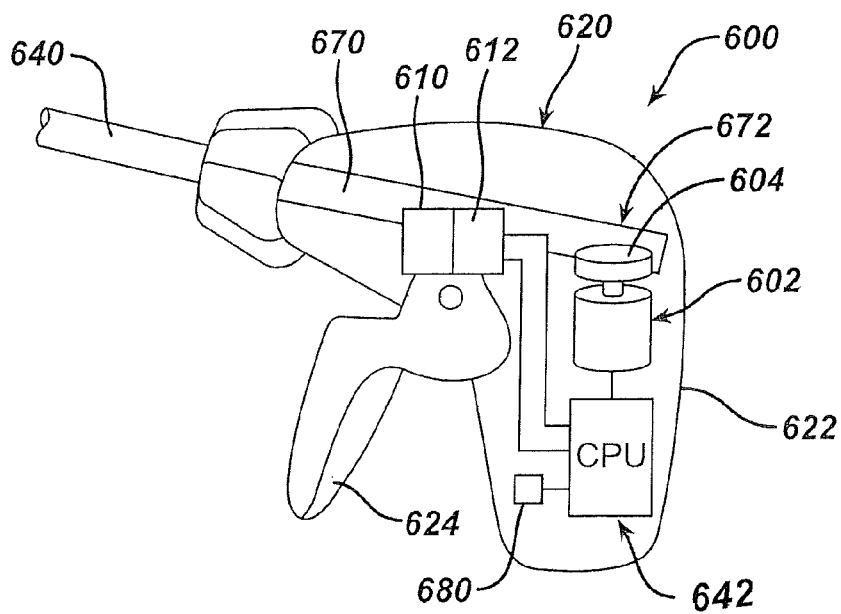
FIG. 13 depicts a partial view of an exemplary electrosurgical device including a motor driven blade and a tactile feedback feature.

FIG. 13 depicts an electrosurgical device (600) comprising a handpiece (620), a shaft (640) extending distally from handpiece (620), and an elongate member (670) slidably disposed in shaft (640). Handpiece (620) includes a pistol grip (622) and a trigger (624). An end effector (not shown), similar to end effectors (50, 150) described elsewhere herein, is disposed at the distal end of shaft (640), and includes a pair of jaws with integral electrodes. Elongate member (670) is similar to elongate member (170) described above. In particular, elongate member (670) has a blade (not shown) and pair of flanges (not shown) at its distal end. Elongate member (670) is movable distally to close the jaws at the end effector and sever tissue clamped between the jaws. A motor (602) is located within handpiece (620). Motor (602) includes an integral drive pinion (604), such that motor (602) is operable to rotate drive pinion (604). The proximal portion of elongate member (670) includes a rack (672) engaged with drive pinion (604). Thus, as drive pinion (604) is rotated by motor (602), elongate member (670) translates longitudinally due to engagement between drive pinion (604) and rack (672).

Electrosurgical device (600) also includes a trigger movement sensor (610), a trigger clutch (612), a control module 642, and a power source (680). Trigger movement sensor (610) of the present example is in communication with trigger (624), such that trigger movement sensor (610) senses movement of trigger (624) toward and away from grip (622). Trigger movement sensor (610) is thus similar to trigger movement sensor (310) described above. Similarly, control module 642 is in communication with trigger movement sensor (610) and motor (602) in a manner similar to the above-described relationship between control module (342), trigger movement sensor (310), and motor (302).

Control module 642 is also in communication with trigger clutch (612). In particular, control module 642 operates trigger clutch (612) in response to one or more conditions detected by control module 642. Trigger clutch (612) is operable to provide tactile feedback to the user through trigger (624), based on control signals from control module 642. For instance, as the user squeezes trigger (624) toward grip (622) and control module 642 senses that the jaws are encountering thick or dense tissue, control module 642 may activate trigger clutch (612) to arrest movement of trigger (624) or provide some other form of tactile feedback through trigger (624), to alert the user that elongate member (670) will not be translating distally until the tissue is sufficiently heated/sealed by the electrodes in the end effector, etc. As another merely illustrative example, trigger clutch (612) may provide resistance to movement of trigger (624), with such resistance being a function of the resistance encountered by distally advancing elongate member (670). The user may thus be able to "feel" the toughness or thickness of the tissue being clamped/cut, yet the resistance provided through trigger clutch (612) may still be less than the resistance that would otherwise be felt if electrosurgical device (600) had a fully manual trigger mechanism (28) like electrosurgical device (10) described above. In some versions, trigger clutch (612) comprises a linear solenoid, a torsional solenoid, or some other type of device.

B. Exemplary Clamping Brake on Trigger

Figure 14:
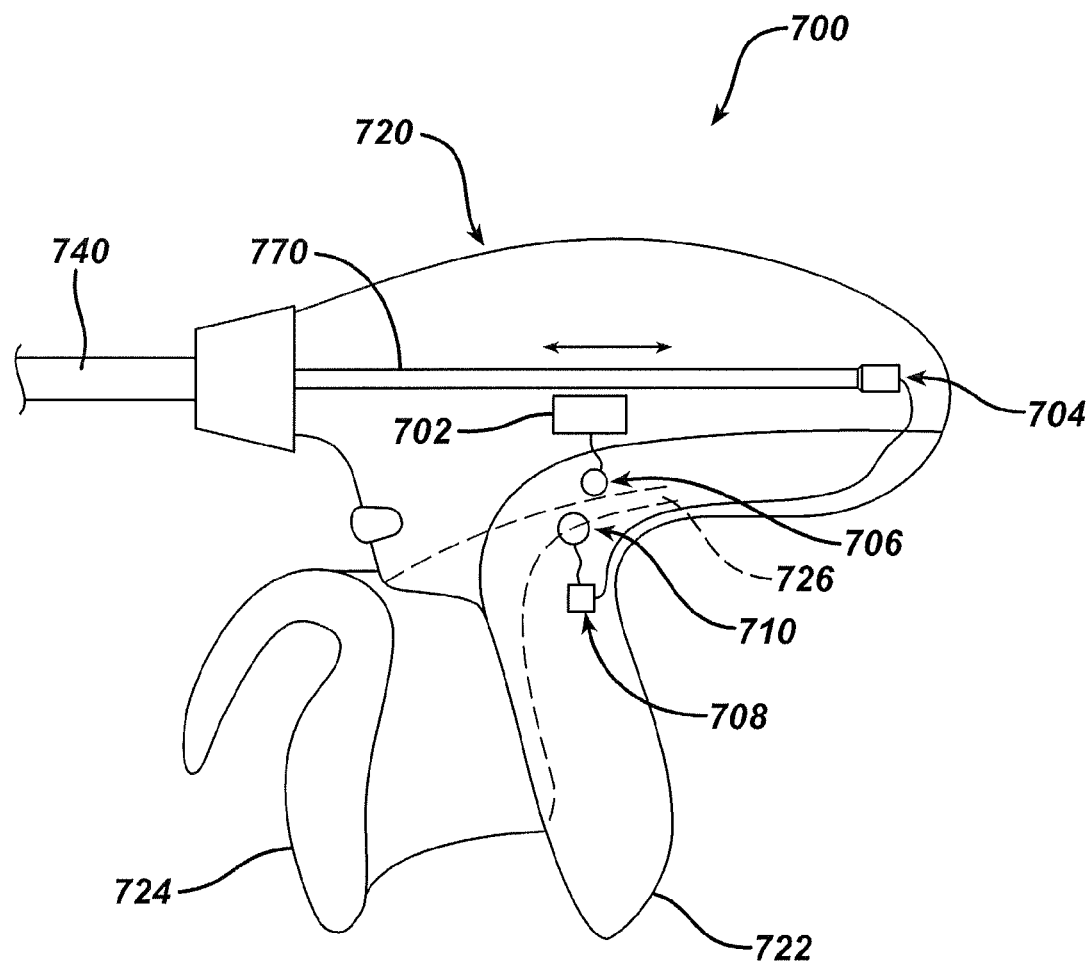
FIG. 14 depicts a partial view of another exemplary electrosurgical device including a motor driven blade and a tactile feedback feature.

FIG. 14 shows another electrosurgical device (700) comprising a handpiece (720), a shaft (740) extending distally from handpiece (720), and an elongate member (770) slidably disposed in shaft (740). Handpiece (720) includes a pistol grip (722) and a trigger (724). An end effector (not shown), similar to end effectors (50, 150) described elsewhere herein, is disposed at the distal end of shaft (740), and includes a pair of jaws with integral electrodes. Elongate member (770) is similar to elongate member (170) described above. In particular, elongate member (770) has a blade (not shown) and pair of flanges (not shown) at its distal end. Elongate member (770) is movable distally to close the jaws at the end effector and sever tissue clamped between the jaws. A motor (702) is located within handpiece (720). Motor (702) is operable to selectively drive elongate member (770) longitudinally, in any manner as described herein or otherwise.

Electrosurgical device (700) also includes a sensor (704), a linear variable differential transformer (LVDT) (706), a servo (708), and a brake (710). Sensor (704) is positioned and configured to measure pressure, force, position, velocity, acceleration, and/or other parameters associated with operation of elongate member (770). Of course, as described elsewhere herein, at least some of such parameters may be monitored by monitoring motor (702) instead. LVDT (706) is coupled with a projection (726), which protrudes rearwardly from trigger (724) and moves unitarily with trigger (724). LVDT (706) is thus operable to sense movement (e.g., position, velocity, acceleration) of trigger (724). Of course, any other suitable type of device may be used to sense movement of trigger (724), including but not limited to various trigger movement sensing devices referred to herein. LVDT (706) is also coupled with motor (702), such that motor (702) is activated based on movement of trigger (724) as sensed by LVDT (706). While LVDT (706) is shown as being connected directly to motor (702), it should be understood that various components (e.g., a control module, etc.) may be communicatively positioned between LVDT (706) and motor (702).

Brake (710) is also coupled with projection (726), and is operable to selectively clamp down on projection (726) with pads (not shown) in order to selectively provide frictional resistance to movement of trigger (724). Brake (710) is communicatively coupled with servo (708), which is operable to drive brake (710), and which is further communicatively coupled with sensor (704). Thus, servo (708) is operable to drive brake (710) based at least in part on operational parameters of elongate member (770). Again, various other components (e.g., control module, etc.) may be communicatively positioned between any of these components (e.g., to store and execute a control algorithm, etc.). It should be understood that, through use of brake (710) and sensor (704), motion of trigger (724) may be variably opposed based at least in part on resistance encountered by advancing elongate member (770). The nature of brake (710) may permit such resistance to be provided on a sliding scale, such as from between little resistance to full resistance, representing or otherwise corresponding with the varied resistance encountered by advancing elongate member (770). As with other tactile feedback features referred to herein, brake (710) may also provide such tactile feedback in real time. In addition, as with other tactile feedback features referred to herein, the resistance provided through brake (710) may still be less than the resistance that would otherwise be felt if electrosurgical device (700) had a fully manual trigger mechanism (28) like electrosurgical device (10) described above.

C. Exemplary ERF Actuator on Trigger

Figure 15:
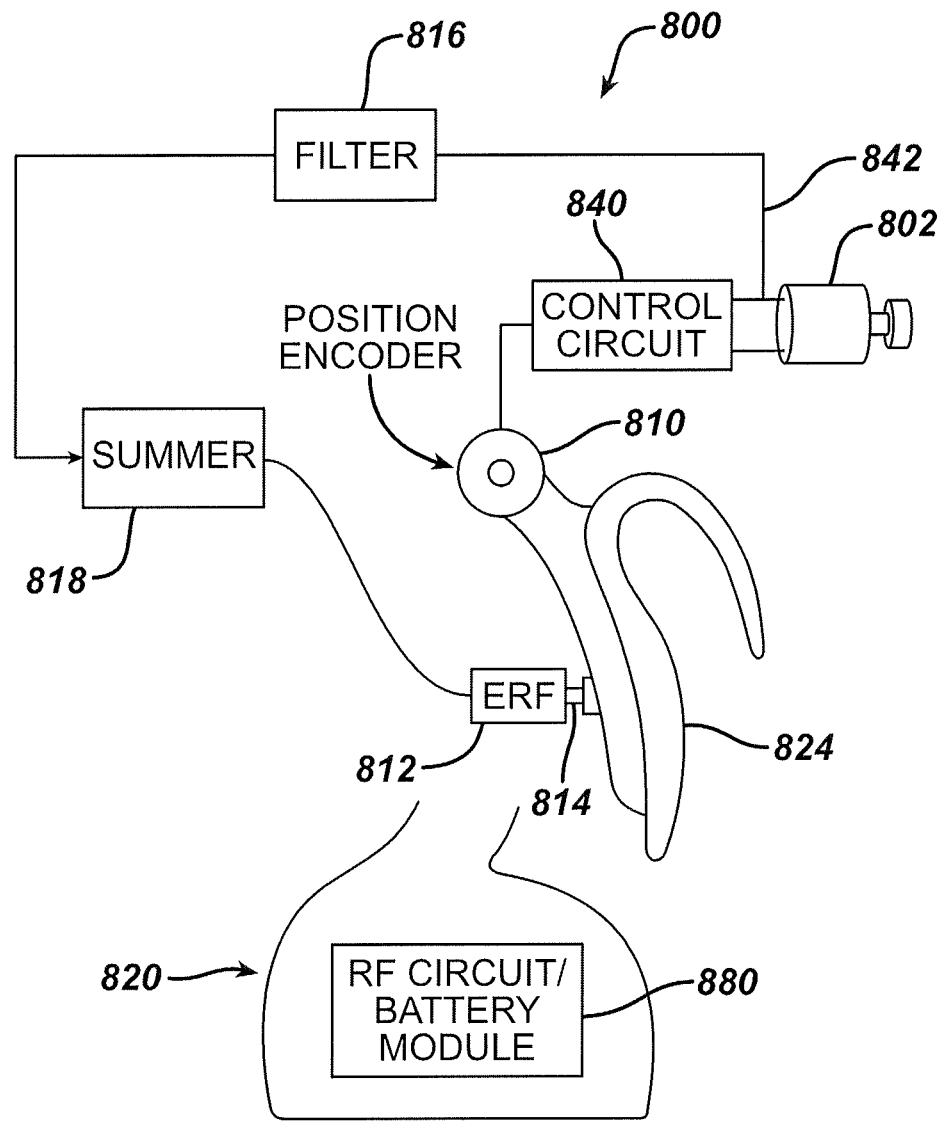
FIG. 15 depicts a partial view of yet another exemplary electrosurgical device including a motor driven blade and a tactile feedback feature.

FIG. 15 shows additional exemplary components of a drive and feedback system (800) that may be used in any electrosurgical device (10, 100, 300, 500, 600, 700) referred to herein. In this example, drive and feedback system (800) includes a motor (802) that is used to drive an elongate member (not shown) that is similar to elongate member (170). System (800) is responsive to movement of a trigger (824), which is similar to triggers (24, 324, 524, 624, 724) described elsewhere herein. System (800) is also powered by a power source (880) that is integral with the handpiece (820) of the electrosurgical device, though it should be understood that an external power source may be used. Power source (880) of this example includes one or more batteries and an RF circuit.

An encoder (810) is coupled with trigger (824) in this example and is operable to sense the position of trigger (824) and thus movement of trigger (824). Again, any other suitable type of sensor may be used to sense the position/movement of trigger (824). The signal from encoder (810) is communicated to a control module (840), which is in further communication with motor (802). Control module (840) thus activates motor (802) based on the position/movement of trigger (824). As is also shown in FIG. 15, a signal communication path (842) is provided from between control module (840) and motor (802) to a filter (816), passing to a summer (818), and then to an electrorheological fluid (ERF) actuator (812). Filter (816) provides a relatively smooth, slowly-varying DC signal that represents that represents the position or number of revolutions of motor (802). Filter (816) differentiates the position information to obtain a velocity of the change in position. In some versions, the velocity is detected directly with a sensor and filter (816) is used to primarily to remove any noise. Summer (818) compares the signal from filter (816) with a desired/predetermined speed to obtain an error signal. ERF actuator (812) includes a piston (814), which is engaged with trigger (824). ERF actuator (812) is operable to selectively drive piston (814) against trigger (824) based on a signal communicated from summer (818). In the present example, this signal represents or corresponds with forces encountered by the elongate member, which translates into mechanical resistance encountered by motor (802), which in turn is discernable through the signal along path (842). For instance, if the speed of motor (802) is above a desired/predetermined speed, then ERF actuator (812) may drive piston (814) against trigger (824) to provide a resistance force against trigger (824). ERF actuator (812) may thereby provide tactile feedback to the surgeon.

It should be understood from the foregoing that, through use of ERF actuator (812) and a signal along pathway (842), motion of trigger (824) may be variably opposed based at least in part on resistance encountered by advancing the elongate member. The nature of ERF actuator (812) may permit such resistance to be provided on a sliding scale, such as from between little resistance to full resistance, representing or otherwise corresponding with the varied resistance encountered by advancing the elongate member. As with other tactile feedback features referred to herein, ERF actuator (812) may also provide such tactile feedback in real time. In addition, as with other tactile feedback features referred to herein, the resistance provided through ERF actuator (812) may still be less than the resistance that would otherwise be felt if the electrosurgical device had a fully manual trigger mechanism (28) like electrosurgical device (10) described above.

IV. EXEMPLARY INCORPORATION OF VISUAL FEEDBACK IN ELECTROSURGICAL DEVICE

Figure 16:
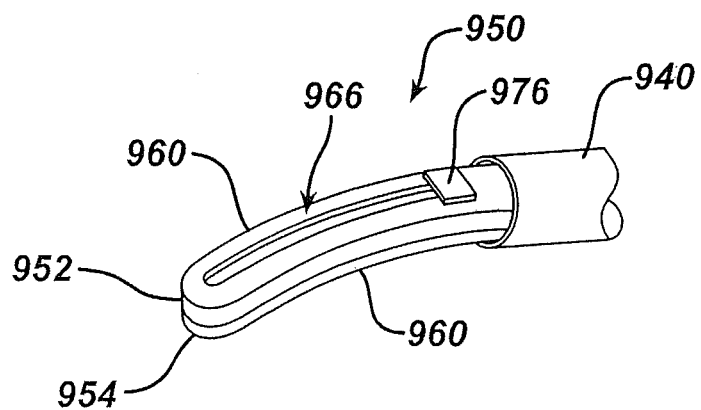
FIG. 16 depicts an end effector of an exemplary electrosurgical device including a photosensitive material.
Figure 17:
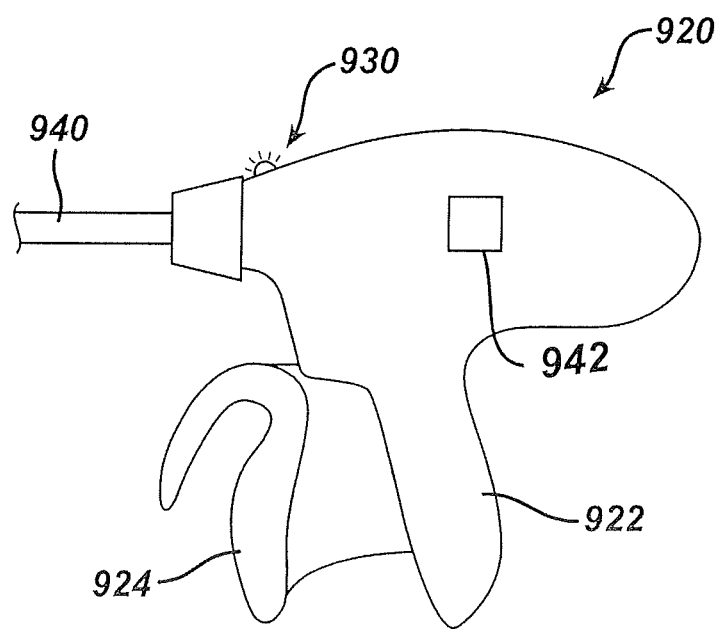
FIG. 17 depicts a handle portion of the electrosurgical device having the end effector of FIG. 16, with a visual feedback feature.

In addition to or as an alternative to providing tactile feedback to a user, it may be desirable in some instances for an electrosurgical device to provide visual feedback to a user. By way of example only, particularly when jaws of an end effector heat up significantly during use, it may be desirable in some instances to alert a user that the outer surfaces of the jaws of the end effector of an electrosurgical device are contacting tissue. This may be desirable to avoid inadvertent burning of tissue at a surgical site. In other words, while it may be desirable in some settings to burn tissue that is clamped between the jaws of the end effector, it may also be desirable to avoid burning tissue that is not clamped between the jaws of the end effector. To that end, FIGS. 16-17 show exemplary features that may be used to alert a user to avoid inadvertently burning tissue with an end effector. Specifically, FIG. 16 shows an end effector (950) disposed at the distal end of a shaft (940). End effector (950) includes an upper jaw (952) and a lower jaw (954), similar to other jaws referred to herein. An elongate slot (966) can be seen in upper jaw (952), similar to slot (56) of jaw (52). In addition, an upper flange (976) of an elongate member can be seen. The elongate member in this example is similar to other elongate members referred to herein.

As shown in FIG. 17, shaft (940) extends distally from a handpiece (920), which includes a pistol grip (922) and a trigger (924) to actuate the elongate member and clamp down with jaws (952, 954). Handpiece (920) also includes an integral control module (942), and may further include an integral power source (not shown). Of course, control module (942) and/or a power source may be provided externally (e.g., in a piece of capital equipment), if desired. Referring back to FIG. 16, a photosensitive material (960) is applied to the exterior of jaws (952, 954). To the extent that end effector (950) is used at an illuminated surgical site, photosensitive material (960) may be able to detect when the exterior of either jaw (952, 954) is placed against tissue, by detecting darkness. In other words, the tissue against the exterior of jaw (952, 954) may cut off the light that would otherwise be imposed on photosensitive material (960). Photosensitive material (960) may further be in communication with control module (942), which may be configured to provide a predetermined response when light levels detected by photosensitive material (960) indicate that the exterior of jaw (952, 954) is against tissue. In particular, control module (942) may activate a light (930) (e.g., a red light) in response to an indication from photosensitive material (960) that the exterior of jaw (952, 954) is against tissue.

In some settings, the exterior of at least one jaw (952, 954) may incidentally fall in a shadow during a surgical procedure, such that the light imposed on photosensitive material (960) is reduced without the exterior of jaw (952, 954) actually contacting tissue. To avoid such a situation creating a "false alarm," control module (942) may be tuned to only activate light (930) after the light level sensed by photosensitive material (960) falls below a certain threshold. An appropriate threshold for this purpose will be apparent to those of ordinary skill in the art in view of the teachings herein.

In addition, control module (942) may be configured to only activate light (930) in response to an indication from photosensitive material (960) that the exterior of jaw (952, 954) is against tissue when one or more other conditions are met. For instance, control module (942) may be configured to provide such a response only when the temperature of either jaw (952, 954) is also beyond a certain threshold. Thus, jaws (952, 954) may further include one or more temperature sensors. In addition or in the alternative, control module (942) may factor in tissue impedance as sensed by electrodes of jaws (952, 954) to determine whether to activate light (930). It should be understood that requiring at least one additional input, beyond just input from photosensitive material (960), may avoid the chances of an unwarranted warning to the user when the exteriors of jaws (952, 954) are not even hot enough to burn adjacent tissue.

Photosensitive material (960) of the present example is configured to generate a voltage in the absence of light, and such a voltage is what may be communicated to control module (942). Alternatively, photosensitive material (960) may be configured to generate a voltage in the presence of light, and control module (942) may be configured to detect drops in such voltage. For instance, photosensitive material (960) may comprise a photovoltaic film. In addition or in the alternative, photosensitive material (960) may comprise a photo resistor (e.g., a cadmium sulfate cell, etc.), a photo transistor, a photo diode, and/or some other type of component. An exemplary photo resistor is the PDV-P9200 from Advanced Photonix, Inc., of Ann Arbor, Mich. An exemplary photo transistor is the SDP8406-003 by Honeywell Sensing and Control of Golden Valley, Minn. An exemplary photo diode is the SMD211-021 by Honeywell Sensing and Control of Golden Valley, Minn. As another merely illustrative example, a circuit including photosensitive material (960) may be configured to provide a relatively high voltage in the absence of light and provide a relatively low voltage in the presence of light. Various suitable materials that may be used for photosensitive material (960) will be apparent to those of ordinary skill in the art in view of the teachings herein. It should also be understood that photosensitive material (960) may be replaced or supplemented with various components and devices that are responsive to light (and/or the absence of light), including but not limited to photoresistors, photovoltaic cells, photodiodes, etc.

While light (930) is used to provide visual feedback to the user, it should be understood that any other suitable form of visual feedback may be provided to the user. In addition or in the alternative, one or more forms of audio feedback may be provided to the user, such as a beep or alarm, etc. An audio feedback device may be driven by control module (942) in a manner similar to that described above with respect to light (930).

It should be understood that the foregoing teachings relating to visual and audio feedback may be readily applied to electrosurgical devices where a movable member (such as the various versions of elongate member referred to herein) is actuated purely manually/mechanically as well as those where the same kind of movable member is actuated electromechanically. Thus, the foregoing teachings relating to visual and audio feedback may be readily applied to any of the electrosurgical devices referred to herein, as well as various other kinds of devices.

V. EXEMPLARY INCORPORATION OF BATTERY PACK IN ELECTROSURGICAL DEVICE

Figure 18A:
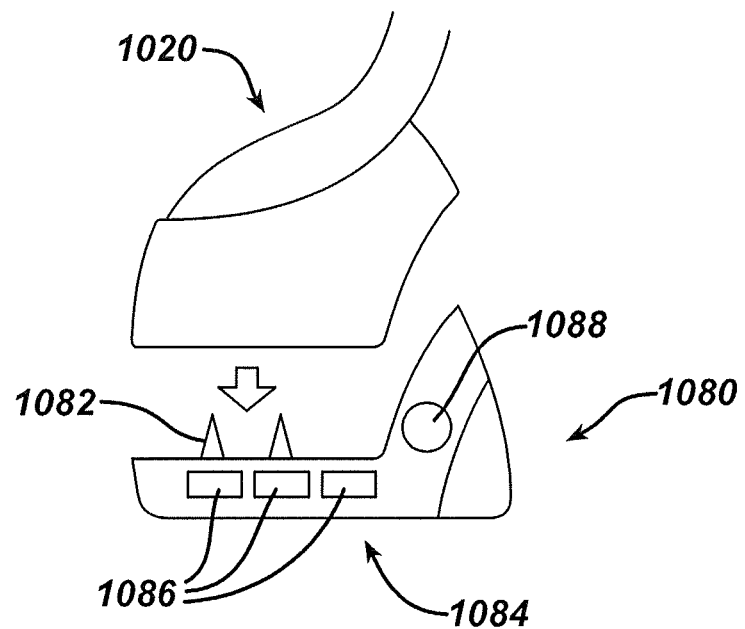
FIG. 18A depicts a handle portion of an electrosurgical device separated from an exemplary battery pack.
Figure 18B:
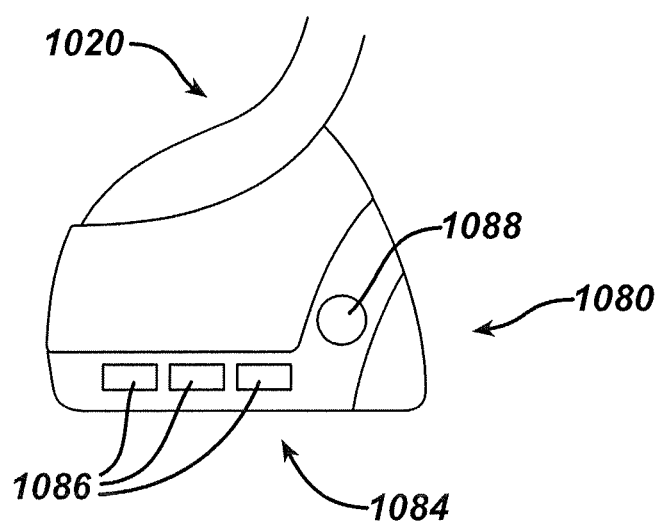
FIG. 18B depicts the handle portion and battery pack of FIG. 18A coupled together.

As noted above, an electrosurgical device may include its own integral power source, in addition to or in lieu of receiving power from a conventional wall outlet or separate piece of capital equipment. FIGS. 18A-18B show a merely illustrative example of how a portable power source may be integrated with an electrosurgical device, such as any of the electrosurgical devices referred to herein (among others). In particular, FIGS. 18A-18B show a handpiece (1020) of an electrosurgical device coupling with a portable battery pack (1080). Battery pack (1080) of this example includes one or more battery cells and a pair of contacts (1082). The battery cells of battery pack (1080) may be rechargeable and may comprise any suitable type of battery, including but not limited to lithium ion batteries (e.g., CR123A type batteries, lithium polymer (LiPo) type batteries, lithium iron phosphate (LiPO4) type batteries, prismatic cell type lithium ion batteries, etc.), alkaline batteries, nickel cadmium batteries, etc. In some versions, the battery cells have a relatively low internal impedance, allowing delivery of relatively high currents from battery pack (1080) without making battery pack (1080) undesirably large and/or without battery pack (1080) getting undesirably hot during normal use. In the present example, battery pack (1080) is configured to store at least 30,000 joules of energy and has a capacity operable to supply current at approximately 5.3 C. In some settings, such a battery pack (1080) may be operable to power approximately 100 tissue transections through an electrosurgical device as described herein, with each transaction delivering or drawing approximately 300 joules of energy.

In addition or in the alternative to battery cells of the type described above, battery pack (1080) may include one or more capacitors, one or more supercapacitors, and/or various other kinds of power sources. Battery pack (1080) is configured to provide power to electrical components of the electrosurgical device through contacts (1082). Battery pack (1080) is also configured to mechanically couple with handpiece (1020), such as through one or more latches, resilient tabs, barbs, clips, clamps, etc.

Battery pack (1080) of the present example further includes an indicator (1084) that is operable to show the charge state of battery pack (1080). It should therefore be understood that battery pack (1080) may further include circuitry (not shown) that is operable to drive indicator (1084). Indicator (1084) of this example comprises three separate LED lights (1086)—green to indicate full, yellow to indicate partially full, and red to indicate depleted. Of course, indicator (1084) may alternatively take a variety of other forms. By way of example only, indicator (1084) may comprise an electrochromic display or any other suitable type of display. While indicator (1084) is part of battery pack (1080) in the present example, it should be understood that indicator (1084) may instead be part of handpiece (1020) and/or any other suitable component.

Battery pack (1080) of the present example further includes an interrogation button (1088). Interrogation button (1088) is operable to selectively activate indicator (1084) to show the charge state of battery pack (1080). Thus, when interrogation button (1088) is not being pressed, indicator (1084) does not show the charge state of battery pack (1080). Interrogation button (1088) may thus conserve power of battery pack (1080). While interrogation button (1088) is part of battery pack (1080) in the present example, it should be understood that interrogation button (1088) may instead be part of handpiece (1020) and/or any other suitable component. Of course, as with indicator (1084), interrogation button (1088) may simply be omitted if desired. For instance, indicator (184) may show the charge state of battery pack (1080) continuously.

Various other suitable ways in which a battery pack (1080) or other source of integral power may be incorporated into an electrosurgical device or other type of device will be apparent to those of ordinary skill in the art in view of the teachings herein.

VI. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An electrosurgical device, comprising:
   (a) a handpiece, wherein the handpiece includes a pivoting trigger;
   (b) a shaft extending distally from the handpiece, the shaft having a distal end;
   (c) an end effector at the distal end of the shaft, the end effector comprising:
      (i) a first jaw, wherein the first jaw includes a first electrode, and
      (ii) a second jaw, wherein the second jaw includes a second electrode,
      wherein the first jaw is movable toward the second jaw to clamp tissue between the first and the second jaws,
      wherein the first and the second electrodes are operable to deliver radiofrequency energy to the tissue clamped between the first and the second jaws;
   (d) a jaw closure feature operable to move the first jaw toward the second jaw;
   (e) an electromechanical driver operable to drive the jaw closure feature to move the first jaw toward the second jaw;
   (f) a sensor configured to sense an operational parameter associated with the jaw closure feature; and
   (g) a braking feature comprising a pair of pads, wherein the braking feature is operable to selectively provide variable frictional resistance against pivotal movement of the pivoting trigger by driving the pair of pads against an exterior surface of the pivoting trigger, wherein the braking feature is operable to vary the frictional resistance based on data from the sensor.

* * * * *